United States Patent [19]

Collier et al.

[11] Patent Number: 5,985,548
[45] Date of Patent: Nov. 16, 1999

[54] AMPLIFICATION OF ASSAY REPORTERS BY NUCLEIC ACID REPLICATION

[75] Inventors: David Nash Collier; Richard Calvin Ebersole, both of Wilmington, Del.; Tina Marie Hatfield, Elkton, Md.; Edwin R. Hendrickson, Hockessin, Del.; John Richard Moran, Charleston, S.C.

[73] Assignee: E. I. du Pont de Nemours and Company, Wilmington, Del.

[21] Appl. No.: 08/256,627

[22] PCT Filed: Feb. 4, 1993

[86] PCT No.: PCT/US93/01281

§ 371 Date: Feb. 13, 1995

§ 102(e) Date: Feb. 13, 1995

[87] PCT Pub. No.: WO93/15229

PCT Pub. Date: Aug. 5, 1993

[51] Int. Cl.$^6$ .............................. C12Q 1/68; C12Q 1/70; C07H 21/04; G01N 33/53

[52] U.S. Cl. ................................ 435/6; 435/5; 435/91.2; 435/7.1; 435/7.2; 435/7.9; 536/24.3; 536/24.32; 536/24.33; 536/26.6

[58] Field of Search .................................. 435/6, 5, 91.2, 435/7.1, 7.9; 536/24.3–24.33, 26.6

[56] References Cited

U.S. PATENT DOCUMENTS

| | | | |
|---|---|---|---|
| 4,668,621 | 5/1987 | Doellgast | 435/13 |
| 4,745,054 | 5/1988 | Rabin et al. | 435/6 |
| 4,882,269 | 11/1989 | Schneider et al. | 435/6 |
| 4,957,858 | 9/1990 | Chu et al. | 435/6 |
| 4,965,188 | 10/1990 | Mullis et al. | 435/6 |
| 4,994,368 | 2/1991 | Goodman et al. | 435/6 |
| 5,200,314 | 4/1993 | Urdea | 435/6 |
| 5,213,961 | 5/1993 | Bunn et al. | 435/6 |

FOREIGN PATENT DOCUMENTS

| | | | |
|---|---|---|---|
| AI 2067909 | 5/1992 | Canada . | |
| 2067909 | 11/1992 | Canada | C12Q 1/68 |
| 0 204 510 | 12/1986 | European Pat. Off. | C12Q 1/68 |
| 0 320 308 | 6/1989 | European Pat. Off. | C12Q 1/68 |
| 0 544 212 | 6/1993 | European Pat. Off. | C12Q 1/68 |
| 304607 | 7/1991 | Japan . | |
| 335580 | 6/1993 | Japan . | |
| WO 87/06270 | 10/1987 | WIPO | C12Q 1/68 |
| WO 89/03891 | 5/1989 | WIPO | C12Q 1/68 |
| WO 89/11546 | 11/1989 | WIPO | C12Q 1/68 |
| WO 90/03445 | 4/1990 | WIPO . | |
| WO 90/11374 | 10/1990 | WIPO | C12Q 1/68 |
| WO 90/14441 | 11/1990 | WIPO . | |
| WO 91/17442 | 11/1991 | WIPO | G01N 33/359 |

OTHER PUBLICATIONS

Kricka, Clin. Chem 40: 347–357, 1994.
Kricka et al. 38:327–328, 1992.
Day et al. Biochem J. 267:119–123, 1990.
Sharkey et al. Bio Technology 12:506–509, 1994.
Sano et al. Science 260:698–699, 1993.
Zhou et a;. Nucleic Acids Research 21: 6038–6039, 1993.
Urdea "A Comparison of Nonradioisotopic Hybridization Assay Methods Using Fluorescent Chemiluminescent and Enzyme Labeled Synthetic Oligodeoxyribonucelotide Probes" NAR 16: 4937–4956, 1988.
Cardullo et al. "Detection of Nucelic Acid Hybridization by Nonradioactive Fluorescence Energy Transfer" PNAS 85: 8790–8794. 1988.
Bobrow, M.N. et al, *Journal of Immunological Methods*, 125, 279–285, (1989).
Sano, T. et al, *Science*, 258, 120–122, Oct. 2, 1992.
Bates, D.L., *Biotechnology*, 5(7), 204–209 (1987).
Vary, C.P.H. et al, *Clin. Chem.*, 32(9), 1696–1701 (1986).
Oellerich, M., *J. Clin.. Chem. Clin. Biochem.*, 22(12), 895–904 (1984).
Ruzicka, V. et al, *Science*, 260, 698–699 (1993).
Zhou, H.R. et al, *Nucleic Acids*, 21(25), 6038–6039 (1993).
Lomell, H. et al, *Clin. Chem.*, 35(9), 1826–1831 (1989).
Corti, A. et al, *Nucleic Acids Res.*, 19(6), 1351 (1991).

*Primary Examiner*—Stephanie W. Zitomer
*Assistant Examiner*—Diane Rees

[57] ABSTRACT

A method for the amplified detection of an analyte, wherein amplification is achieved by replication of a target nucleic acid sequence which has been immobilized in response to analyte.

27 Claims, 7 Drawing Sheets

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 75 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

ATGCGTAGCA GCTTTACCGC AGAGATCATG CCTATGTACC ATGCTATCCT ACCTGTAAGT    60

CATAGCTGTT TCCTG    75

(2) INFORMATION FOR SEQ ID NO:2:

(i) SEQUENCE CHARACTERISTICS:
      (A) LENGTH: 75 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

CAGGAAACAG CTATGACTTA CAGGTAGGAT AGCATGGTAC ATAGGCATGA TCTCTGCGGT    60

AAAGCTGCTA CGCAT    75

(2) INFORMATION FOR SEQ ID NO:3:

(i) SEQUENCE CHARACTERISTICS:
      (A) LENGTH: 75 base pairs
      (B) TYPE: nucleic acid
      (C) STRANDEDNESS: single
      (D) TOPOLOGY: linear (ii) MOLECULE TYPE:  DNA (genomic)

(xi) SEQUENCE DESCRIPTION:  SEQ ID NO:3:

ATGCGTAGCA GCTTTACCGC AGAGATCATG CCTATGTACC ATGCTATCCT ACCTGTAAGT          60

AAAGCTGCTA CGCAT          75

(2) INFORMATION FOR SEQ ID NO:4:

(i) SEQUENCE CHARACTERISTICS:
            (A) LENGTH:  75 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:4:

ATGCGTAGCA GCTTTACTTA CAGGTAGGAT AGCATGGTAC ATAGGCATGA TCTCTGCGGT          60

AAAGCTGCTA CGCAT          75

(2) INFORMATION FOR SEQ ID NO:5:

(i) SEQUENCE CHARACTERISTICS:
            (A) LENGTH:  17 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:5:

ATGCGTAGCA GCTTTAC          17

(2) INFORMATION FOR SEQ ID NO:6:

(i) SEQUENCE CHARACTERISTICS:
            (A) LENGTH:  17 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:6:

CAGGAAACAG CTATGAC          17

(2) INFORMATION FOR SEQ ID NO:7:

(i) SEQUENCE CHARACTERISTICS:
            (A) LENGTH:  75 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:7:

ATGCGTAGCA GCTTTACCGC AGAGATCATG CCTATGTACC ATGCTATCCT ACCTGTAATA          60

GTAGAAACAG CTGAC          75

(2) INFORMATION FOR SEQ ID NO:8:

(i) SEQUENCE CHARACTERISTICS:
            (A) LENGTH:  75 base pairs
            (B) TYPE:  nucleic acid
            (C) STRANDEDNESS:  single
            (D) TOPOLOGY:  linear -continued (ii) MOLECULE TYPE: DNA (genomic)

(xi) SEQUENCE DESCRIPTION: SEQ ID NO:8:

GTCAGCTGTT TCTACTATTA CAGGTAGGAT AGCATGGTAC ATAGGCATGA TCTCTGCGGT    60

AAAGCTGCTA CGCAT    75

(2) INFORMATION FOR SEQ ID NO:9:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGCAGGAAGA CAAACACTGG CTGGTCTGTG GTGCTGTGCT TGTTCCCCTG TCCTAGTATT    60

GTTTTCTGGG TTGGT    75

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

ACCAACCCAG AAAACAA    17

(2) INFORMATION FOR SEQ ID NO:11:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ACCAACCCAG AAAACAATAC TAGGACAGGG GAACAAGCAC AGCACCACAG ACCAGCCAGT    60

GTTTGTCTTC CTGCC    75

(2) INFORMATION FOR SEQ ID NO:12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGCAGGAAGA CAAACA    16

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single

```
            (D) TOPOLOGY:  linear (ii) MOLECULE TYPE:  DNA (genomic)

(xi) SEQUENCE DESCRIPTION:  SEQ ID NO:13:

GTCAGCTGTT TCTACTA                                                         17
```

AMPLIFICATION OF ASSAY REPORTERS BY NUCLEIC ACID REPLICATION

This application is a 371 of PCT/US 93/01281 filed on Feb. 4, 1993.

FIELD OF THE INVENTION

This invention relates to a method for the amplified detection of an analyte in fluid, wherein amplification is achieved by replicating a target nucleic acid sequence which has been immobilized in response to analyte.

BACKGROUND OF THE INVENTION

The introduction of immunoassays in the 1960s and 1970s greatly increased the number of analytes amenable to precise and accurate measurement. Radio immunoassays (RIAs) and immunoradiometric (IRMA) assays utilize radioisotopic labeling of either an antibody or a competing antigen to measure an analyte. Detection systems based on enzymes or fluorescent labels were then developed as an alternative to isotopic detection systems. D. L. Bates, *Trends in Biotechnology*, 5(7), 204 (1987), describes one such method based upon enzyme amplification. In this method a secondary enzyme system is coupled to a primary enzyme label, for example, the primary enzyme can be linked catalytically to an additional system such as a substrate cycle or an enzyme cascade. Enzyme amplification results from the coupling of catalytic processes, either by direct modification or by interaction with the product of the controlling enzyme.

U.S. Pat. No. 4,668,621 describes utilization of an enzyme-linked coagulation assay (ELCA) in an amplified immunoassay using a clotting cascade to enhance sensitivity. The process involves clot formation due to thrombin activated fibrin formation from soluble fibrinogen and labeled solubilized fibrinogen. Amplification of the amount of reportable ligand attached to solid phase is obtained only by combining use of clotting factor conjugates with subsequent coagulation cascade reactions.

Substrate/cofactor cycling is another variation of enzyme-mediated amplification, and is based on the cycling of a cofactor or substrate which is generated by a primary enzyme label. The product of the primary enzyme is a catalytic activator of an amplifier cycle which responds in proportion to the concentration of substrate and hence the concentration of the enzyme label. An example of this type of substrate cycling system is described in U.S. Pat. No. 4,745,054.

Vary et al., *Clin Chem.*, 32, 1696 (1986) describes an enzyme amplification method suited to nucleic acid detection. This method is a strand displacement assay which uses the unique ability of a polynucleotide to act as a substrate label which can be released by a phosphorylase.

Bobrow et al., *J. of Immunol. Methods*, 125, 279 (1989) discloses a method to improve detection or quantitation of an analyte by catalyzed reporter deposition. Amplification of the detector signal is achieved by activating a conjugate consisting of a detectably labeled substrate specific for the enzyme system, wherein said conjugate then reacts with the analyte-dependent enzyme activation system to form an activated conjugate which deposits wherever receptor for the conjugate is immobilized.

Nucleotide hybridization assays have been developed as a means for detection of specific nucleic acid sequences. U.S. Pat. No. 4,882,269 discloses an amplified nucleic acid hybridization assay in which a target nucleic acid is contacted with a complementary primary probe having a polymeric tail. A plurality of second signal-generating probes capable of binding to the polymeric tail are added to achieve amplified detection of the target nucleic acid. Variations of this methodology are disclosed in PCT Application WO 89/03891 and European Patent Application 204510, which describe hybridization assays in which amplifier or multimer oligonucleotides are hybridized to a single-stranded nucleic acid unit which has been bound to the targeted nucleic acid segment. Signal amplification is accomplished by hybridizing signal-emitting nucleic acid bases to these amplifier and multimer strands. In all of these disclosures amplification is achieved by mechanisms which immobilize additional sites for attachment of signal-emitting probes.

In contrast, the present invention utilizes a fundamentally different concept in achieving signal amplification. In response to analyte, a target nucleic acid sequence is immobilized and replicated using nucleic acid replication techniques. Signal enhancement is achieved by generating and detecting replicates of the target sequence.

U.S. Pat. No. 4,994,368 discloses a nucleic acid hybridization assay which accomplishes detection of polynucleotide analytes by producing replicated copies of a primary polynucleotide sequence. The target sequence of interest is first restricted to provide a free 3' OH end, and then is hybridized to a complementary binding sequence located at the 3' end of two or more template sequences in a single-stranded pattern polynucleotide. Chain extension is performed on the target sequence, and this extension product is then cleaved into fragments which are subsequently hybridized with single-stranded pattern nucleotide. The polymerization, cleavage, rehybridization, polymerization cycle is repeated until a detectable number of copies have been obtained. In a similar vein, PCT application WO 90/0345 describes a nucleic acid detection assay wherein the reporter molecule is an adduct comprising 1) an oligonucleotide probe sequence which is complementary to the targeted site; 2) a primer sequence capable of initiating primer extension; and 3) a sequence segment which is complementary to the primer sequence. As initially added to the test nucleic acid sample, the adduct assumes a hairpin structure which renders the primer inactive. Upon hybridization of the adduct to a target sequence in the sample, however, the adduct becomes activated and its primer sequence becomes available for initiating a primer extension product. The art methods differ from that of Applicants' in that the art uses significantly different and more cumbersome approaches to producing multiple copies of a detectable nucleic acid. Also, these methods are limited to the detection of nucleotide sequences, while Applicants' method is applicable to a wide range of analytes.

The use of RNA as a reporter for immunolocical assays has been described in the literature. WO 87/06270 teaches the use of an RNA capable of being autocatalytically replicated by an RNA-dependent RNA polymerase as a reporter for assaying biopolymers by immunoassay or by nucleic acid probe hybridization.

Similarly WO 91/17442 describes various protein/nucleic acid hybrid probes which can be used to amplify the detectable signal in immunoassays. Signal is amplified by a method comprising first immobilizing an antigenic analyte on a solid substrate, binding to the analyte a protein/nucleic acid hybrid probe comprising a double-stranded RNA T7 polymerase promoter operably connected to either a single-stranded or double-stranded nucleic acid template, removing any unbound probe, transcribing multiple copies of RNA oligomers and detecting and quantifying the transcripts. Template replication is on the order of $10^1$ to $10^4$ copies per template.

The above methods are useful for enhancing the level of detection of analytes by immunoassay, however, both methods suffer from significant restrictions. For example, both methods rely on the use of RNA-dependent polymerases for nucleic acid replication which gives inherently less amplification than other nucleic acid amplification methods such as Polymerase Chain Reaction (PCR) or Ligase Chain Reaction (LCR), and does not result in a molecularly-defined product. It is well known in the art that PCR, for example, will give amplification on the order of $10^6$ to $10^{14}$ copies per target of discreet length. Furthermore, the above methods are not easily adapted to the detection of more than one analyte in a sample.

Sano et al. *Science,* 258, 120, (1992) describes an antigen detection system, termed Immuno-PCR, in which a specific DNA molecule is used as a reporter. A streptavidin-protein A chimera was used to attach a biotinylated DNA to antigen-monoclonal antibody complex that had been immobilized on microtiter plate wells. A segment of the complexed DNA was amplified by Polymerase Chain Reaction (PCR) and the PCR products were analyzed by gel electrophoresis. This method is limited by the need for multiple reagent additions and extensive washing requirements.

SUMMARY OF THE INVENTION

Applicants disclose a sensitive method for detecting an analyte by amplifying the detectable response of an analyte-dependent reporter system. The amplification is achieved using nucleic acid replication of a target nucleic acid sequence after said target sequence has been immobilized in response to the presence of an analyte.

The invention is an amplified detection method for the detection and quantitation of an analyte in a fluid sample. The method comprises first immobilizing an analyte to form what Applicants have termed an "analyte-dependent reporter system" (ADRS). The ADRS will be comprised of a target nucleic acid sequence which has been immobilized in response to the presence of analyte in the sample. Next, the immobilized target nucleic acid sequence of the ADRS is contacted with a nucleic acid replication composition under conditions wherein the target sequence may be replicated, and replication of the target is carried out. And finally, the replicated target nucleic acid sequences are detected, whereby the presence of analyte may be determined.

Applicants' amplified detection method may be specifically designed to be practiced in a number of different ways. For example, Applicants have presented four possible variations of the method (see FIGS. 1, 2, 3, and 6).

In a preferred embodiment of Applicants' method, reference nucleic acid sequences which are different from the target sequences would be included with the ADRS at one or more steps and replicated concurrently with the target sequences under the assay conditions of that method. These reference sequences will be designed to generate sequences which are detectably distinct from the replicated target sequences, and will therefore serve as measures of internal control for each particular assay methodology.

In another preferred embodiment, which is illustrated in FIGS. 4 and 5, the method can be used to detect several analytes within one sample by varying the length of the "variable segment" of the target nucleic acid used in the reporter conjugate for each analyte. In this way, the same primers may be used for all replications within one sample, and size separation of the replicated nucleic acid targets will enable convenient detection of multiple analytes in one sample.

In still another embodiment, which is illustrated in FIG. 6, a convenient variation of the method is disclosed wherein a ligand reporter conjugate is used to compete with sample analytes for binding sites on the capture reagent. Target segments on the unbound ligand reporter conjugates may then be replicated, indicating the presence of analytes in the sample.

DETAILED DESCRIPTION OF THE INVENTION

Applicants disclose a sensitive method for detecting an analyte by amplifying the detectable response of an analyte-dependent reporter system. The amplification is achieved using nucleic acid replication of a target nucleic acid sequence in response to the presence of an analyte.

The present invention provides a method for amplifying the response of an analyte-dependent reporter complex (ADRC). The ADRC is formed in response to analyte and contains the bound analyte. The ADRC may directly immobilize a target nucleic acid, or may react with other reagents to ultimately result in target nucleic acid sequences which are immobilized onto receptors. The resulting product is a nucleic acid replication system which is capable of forming many copies of a target nucleic acid sequence when the proper replication reagents are added. The whole immobilized replication system is referred to by Applicants as the analyte-dependent reporter system (ADRS). Copies of the resulting amplified nucleic acids from the ADRS may be detected, providing a means which is useful for the detection and measurement of analytes in test fluid.

The term "analyte" will refer to a substance to be detected or assayed by the method of the present invention. Typical analytes may include, but are not limited to proteins, peptides, nucleic acid segments, molecules, cells, microorganisms and fragments and products thereof, or any substance for which attachment sites, binding members or receptors (such as antibodies) can be developed.

The term "analyte-dependent reporter system" (ADRS) refers to an immobilized system which is formed in response to the presence of an analyte. The system will contain an immobilized nucleic acid target sequence. The analyte is subsequently detected or quantitated by detection of amplified copies of this target nucleic acid sequence.

The term "analyte-dependent reporter complex" (ADRC) refers to one component of the above system. The ADRC refers to an immobilized analyte capture reagent, an analyte, and a reporter conjugate.

The term "immobilized capture reagent" refers to any substance capable of binding an analyte, such as an antibody, receptor, lectin, nucleic acid or binding protein, which has been immobilized by attachment to an appropriate support. Also, in some instances, the immobilized capture reagent may simply be comprised of a solid support matrix to which an analyte may bind without the aide of an intermediary substance.

Figure 1:
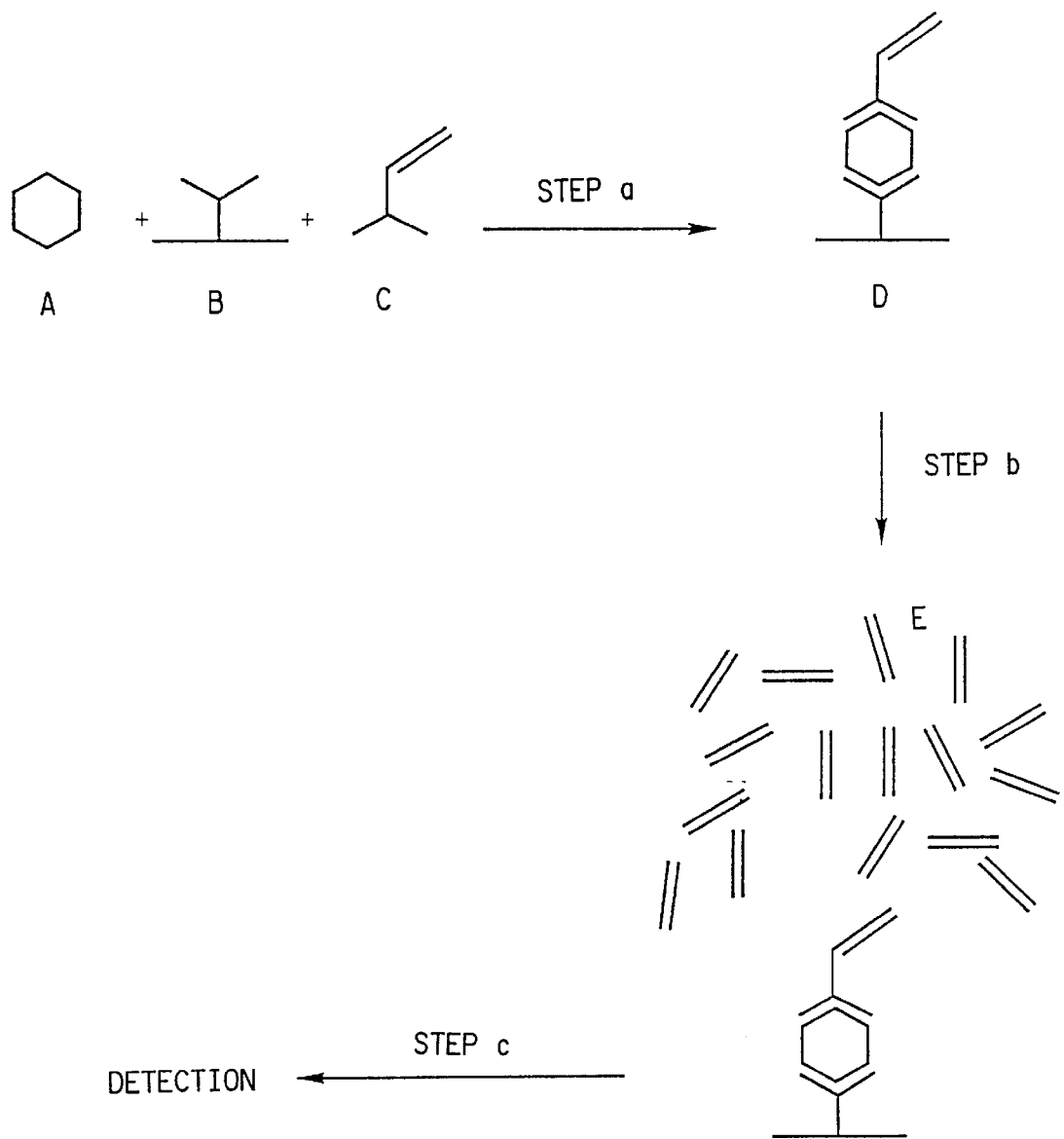
FIG. 1 illustrates the "Direct Target Deposition Method" of amplifying the response of an analyte-dependent reporter system.
Figure 2:
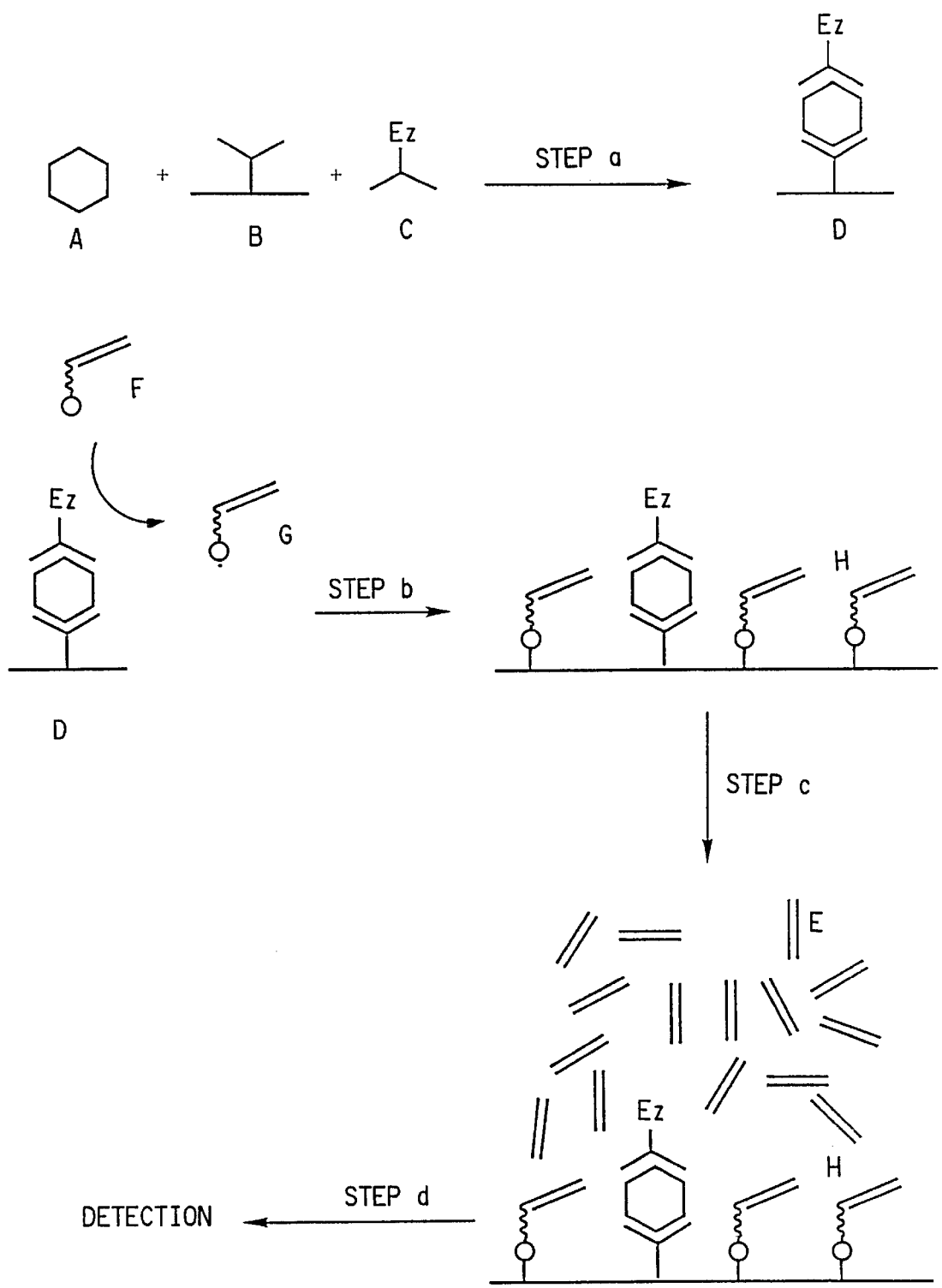
FIG. 2 illustrates the "Catalyzed Target Deposition Method" of amplifying the response of an analyte-dependent reporter system.
Figure 3:
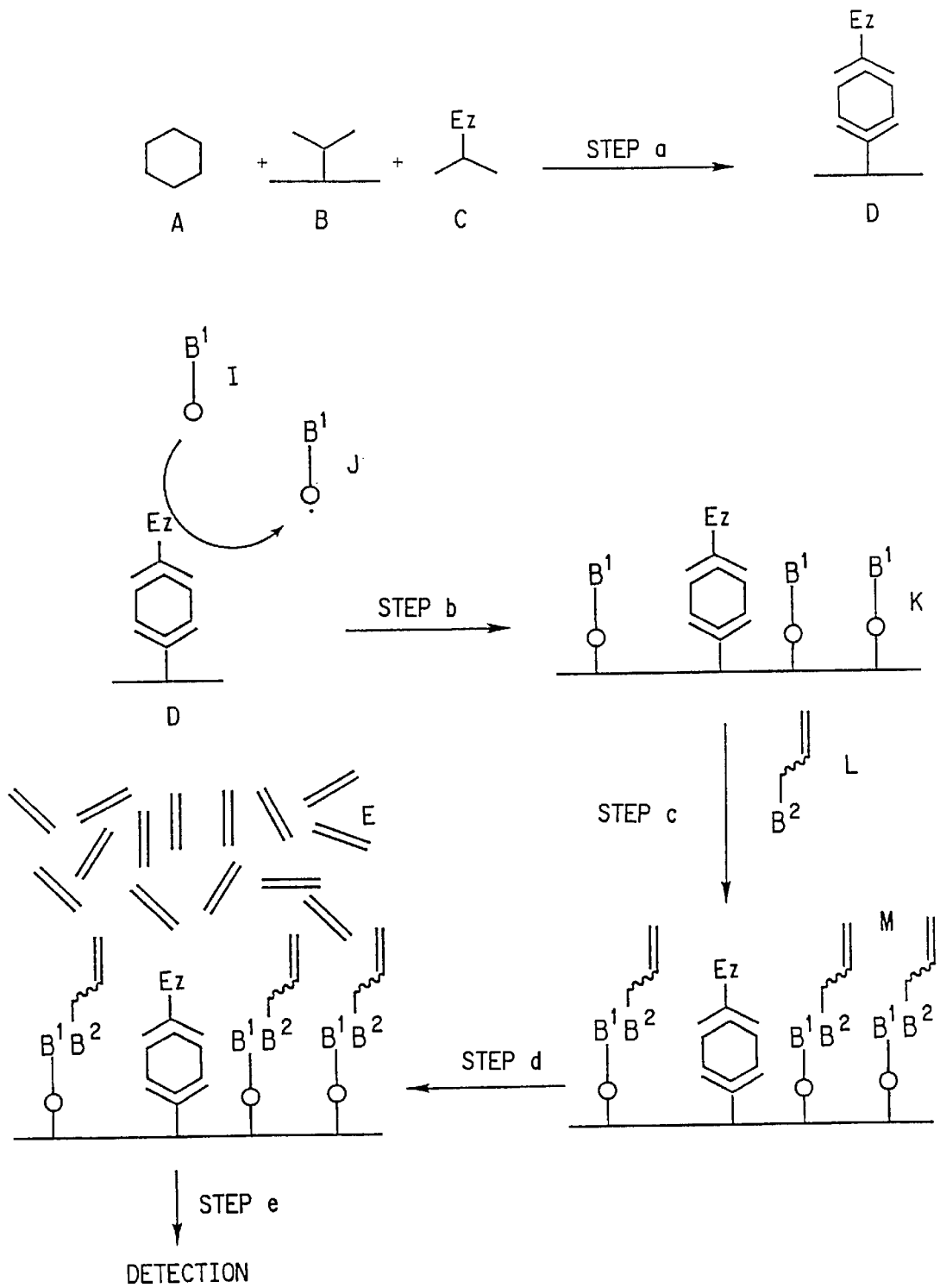
FIG. 3 illustrates the "Catalyzed Indirect Target Deposition Method" of amplifying an analyte-dependent reporter system.

The term "reporter conjugate" refers to either: 1) a conjugate comprising a target nucleic acid sequence coupled to one member of a binding pair such as an antibody, lectin, receptor or binding protein or other moiety which can bind to analyte (as in FIG. 1); or alternatively 2) to a conjugate comprising an enzyme coupled to one member of a binding pair such as an antibody, lectin, receptor or binding protein (as in FIGS. 2 and 3).

The term "target nucleic acid sequence" or "target sequence" or "target" refers to the template nucleic acid within the ADRS which will be replicated to generate replicated nucleic acid target sequences.

The term "nucleic acid replication composition" refers to a composition comprising the ingredients necessary for performing nucleic acid replication. Applicants contemplate that replication may be accomplished by any of several schemes known in this art, including but not limited to the polymerase chain reaction (PCR); or the ligase chain reaction (LCR). If PCR methodology is selected, the replication composition would include for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.), which are hereby incorporated by reference. If LCR methodology is selected, then the nucleic acid replication compositions would comprise, for example, a thermostable ligase, e.g., *T. aquaticus* ligase, two sets of adjacent oligonucleotides wherein one member of each set is complementary to each of the target strands, Tris HCl buffer, KCl, EDTA, NAD, dithiothreitol and salmon sperm DNA. See, for example, Tabor, S. and Richardson, C. C. (1985) *Proc. Acad. Sci. USA* 82, 1074–1078), which is hereby incorporated by reference.

The term "replicated target sequence" refers to the copies of the target nucleic acid sequence produced in the replication process.

The term "nucleic acid replication substrate" refers to a conjugate comprising a target nucleic acid sequence connected, optionally via a spacer, to a moiety capable of activation by an enzyme.

The term "activated nucleic acid replication intermediate" refers to the product obtained from reaction of the nucleic acid replication substrate with the enzyme of the ADRC.

The term "deposited nucleic acid replication product" refers to the product resulting from deposition of the activated nucleic acid replication intermediate onto a receptor.

The term "deposit" or "deposition" means directed binding to an immobilized receptor. Such deposition may result for example, from formation of a covalent bond, direct binding to a solid matrix, or from a specific binding pair interaction.

The term "receptor" means any site which will bind to an activated conjugate of the ADRS, either through the formation of a covalent bond or through a specific binding pair interaction. For example, in Schemes II and III (see FIGS. 1 and 2), the receptors for the activated conjugates of step 2 may be located on the same support which immobilizes the ADRC (as shown); or alternatively, the receptors for the activated conjugates of step 2 may be located on different insoluble supports.

The term "binding substrate" refers to a conjugate comprising a first member of a binding pair species, optionally a spacer, and a moiety capable of being activated by an enzyme.

The term "binding pair" includes any of the class of immune-type binding pairs, such as antigen/antibody or hapten/anti-hapten systems; and also any of the class of nonimmune-type binding pairs, such as biotin/avidin; biotin/streptavidin; folic acid/folate binding protein; complementary nucleic acid segments; protein A or G/immunoglobulins; and binding pairs which form covalent bonds, such as sulfhydryl reactive groups including maleimides and haloacetyl derivatives, and amine reactive groups such as isotriocyanates, succinimidyl esters and sulfonyl halides.

The term "activated binding intermediate" refers to the product obtained from reaction of the binding substrate with the enzyme of the ADRC.

The term "deposited binding product" refers to an activated binding intermediate which has been deposited onto a receptor.

The term "nucleic acid replication conjugate" refers to a conjugate comprising a second member of a binding pair species, optionally a spacer, and a target nucleic acid sequence.

The term "nucleic acid replication binding pair complex" refers to the complex formed between the deposited binding product and the nucleic acid replication conjugate.

The term "replication control" refers to a mixture comprising a reference nucleic acid sequence and a cognate set of primers which have been designed to facilitate nucleic acid replication of the reference sequence.

The term "reference nucleic acid sequence" or "reference sequence" refers to a template nucleic acid that is different from the target nucleic acid sequence. The reference sequence may be incorporated within the ADRS and additionally replicated to serve as an assay control which improves quantitation.

The term "reference nucleic acid conjugate" refers to a conjugate comprising a reference nucleic acid sequence, optionally a spacer, and the analyte or analyte equivalent.

The term "signal-generating nucleic acids" refers to any nucleic acid which has been modified or labeled with a moiety capable of detection via enzymatic means or energy emission; including, but not limited to, fluorescent moieties, radioactive tags, or light-emitting moieties.

The term "primer" refers to a nucleic acid sequence that is complementary to a portion of at least one strand of the targeted nucleic acid and whose purpose is to sponsor and direct nucleic acid replication of the targeted sequence. Primers are designed to be complementary to specific segments of the target or reference sequences, and may be used in combination with another primer, thus forming a "primer set" or "primer pair". Requirements for primer size, base sequence, complementarity and target interaction are discussed in the primer section of the detailed description of the invention. The term "primer", as such, is used generally herein by Applicants to encompass any sequence-binding oligonucleotide which functions to initiate the nucleic acid replication process; such replication processes may include, for example, PCR, LCR or other enzymatic reactions which employ single rather than multiple oligonucleotide initiators.

The phrase "replicated nucleic acid sequences" or "replicated sequences" refers to the nucleic acid replication products produced within the ADRS assay scheme, and is used within this context to include both replicated target sequences and replicated reference sequences.

The term "ligand" will refer to one member of an analyte specific binding pair such as a molecule, protein, peptide, nucleic acid segment, therapeutic agents, polypeptide, toxin, nucleotide, carbohydrate, cell, microorganism, antibody, lectin, receptor, binding protein or chemical agent that is either identical to or structurally related to an analyte, and is capable of binding to the second member of the analyte specific binding pair. The ligand may be structurally modified to enable chemical attachment.

The term "ligand reporter conjugate" refers to a conjugate comprising a target nucleic acid sequence coupled to a ligand. The ligand may be coupled either at the 3' end, the 5' end or at any position between the 3' and 5' ends of the target. Additionally, the ligand is capable of competing with sample analytes for analyte binding sites on an immobilized capture reagent.

The term "immobilized analyte complex" refers to a complex formed between an analyte and an immobilized capture reagent.

The present invention provides an amplified detection method for the detection and quantitation of an analyte in a sample. The method comprises, at step i) immobilizing an analyte to form what Applicants have termed an "analyte-dependent reporter system" (ADRS). The ADRS will be comprised of an immobilized target nucleic acid sequence which has been immobilized in response to the presence of an analyte in the sample. Next, at step ii) the target nucleic acid sequence of the ADRS is contacted with a nucleic acid replication composition under conditions wherein the target sequence may be replicated. At step iii) the target sequences are replicated. Any of several known methods for replication of nucleic acids may be employed. The replication composition which is added will be comprised of the reagents necessary for replication of the target sequence. And finally, at step iv) the replicated target nucleic acid sequences are detected, whereby the presence of analyte may be determined. The replicated target nucleic acid sequences may be detected using any of a number of currently available reporter detection schemes; such as size differentiation, ligand capture, radioactive detection, luminescence detection, fluorophorescence detection, or any combination thereof; including wherein any of these detection schemes may be enzymatically mediated.

Applicants' amplified detection method may be specifically designed to be practiced in a number of different ways. For example, Applicants have presented four possible variations of the method (see FIGS. 1, 2, 3, and 6) which differ in the manner in which the target sequence is ultimately formed within the ADRS.

Multiple target nucleic acid reagents can be used simultaneously within an assay for the detection of different analytes, or to provide assay controls. In a preferred embodiment of Applicants' method, reference nucleic acid sequences which are different from the target sequence would be included within the ADRS at one or more steps and replicated concurrently with the target sequence under the assay conditions of that method. These reference sequences would be designed to generate sequences which are detectably distinct from the replicated target sequences, and would therefore serve as measures of internal control for each particular assay methodology.

In another preferred embodiment, multiple target nucleic acid reagents, each specific for a separate analyte can be employed together in the same assay milieu to facilitate simultaneous detection of multiple analytes.

One embodiment of the present invention, termed the "Direct Target Deposition Method", is illustrated in FIG. 1.

In Step a of this embodiment, the test sample containing the analyte (A) is first reacted with an immobilized capture reagent (B), such as an antibody, and then with a reporter conjugate comprising a target nucleic acid sequence (C) to form an analyte dependent reporter complex (ADRC) (D) from which excess reagents are removed by washing. In Step b, the ADRC is contacted with a nucleic acid replication composition and a replication process is performed to produce replicated nucleic acids (E). In Step c, the replicated nucleic acids are detected. In this embodiment, the reporter conjugate is a conjugate comprising a target nucleic acid sequence and, for example, an antibody or other analyte binding reagent.

An obvious variation of the method, which is easily practiced by one skilled in this art, is an adaption wherein after step a, any excess, nonimmobilized reporter conjugate remaining free in solution would be separated from the immobilized capture reagent-analyte complex. This amount of excess, nonimmobilized reporter conjugate remaining free in the analyte sample would be proportional to the amount of analyte initially present in the sample. This nonimmobilized reporter conjugate, after separation from the bound analyte complexes, could then be replicated while free in solution, for example, and the replicated nucleic acids are detected whereby the presence of analyte in the sample is determined.

Another embodiment of the present invention, termed the "Catalyzed Target Deposition Method", is illustrated in FIG. 2. In Step a of this embodiment, the test sample containing the analyte (A) is first reacted with an immobilized capture reagent (B), such as an antibody, and then with a reporter conjugate (C) to form an analyte dependent reporter complex (D) from which excess reagents are removed by washing. In this embodiment the reporter conjugate (C) is comprised of an enzyme capable of activating a moiety on the nucleic acid replication substrate (F) (such as horseradish peroxidase) and a member of a binding pair (such as an antibody). In Step b, the ADRC formed in Step a is reacted with a nucleic acid replication substrate (F), which contains the target nucleic acid sequence, to form an activated nucleic acid replication intermediate (G), which deposits wherever receptor for the activated nucleic acid replication intermediate is immobilized to produce a deposited nucleic acid replication product (H). Excess reagents are then washed off. In Step c, the deposited nucleic acid Replication product is contacted with a nucleic acid replication composition to produce replicated target sequence nucleic acids (E). In Step d, the replicated nucleic acids are detected.

Another embodiment of the present invention, termed the "Catalyzed Indirect Target Deposition Method", is illustrated in FIG. 3. In Step a of this embodiment, the test sample containing the analyte (A) is first reacted with an immobilized capture reagent (B) (such as an antibody), and then with a reporter conjugate (C) to form an analyte-dependent reporter complex (D) from which excess reagents are removed by washing. In this embodiment the reporter conjugate (C) is comprised of an enzyme (such as horseradish peroxidase) which is capable of activating a moiety on the binding substrate (I). (I), the binding substrate, is a conjugate comprised of this substrate and a member of a binding pair. In Step b, the ADRC is reacted with the binding substrate (I) to form an activated binding intermediate (J) which deposits wherever receptor for the activated binding intermediate is immobilized, to produce a deposited binding product (K). Excess reagents are then washed off. In Step c, the deposited binding product is reacted with a nucleic acid replication conjugate (L), which contains the target nucleic acid sequence and the second member of the binding pair, to produce a nucleic acid replication binding pair complex (M). Excess reagents are then washed off. In Step d, the nucleic acid replication binding pair complex is contacted with a nucleic acid replication composition to produce replicated target sequence nucleic acids (E). In Step e, these nucleic acids are detected.

Figure 4:
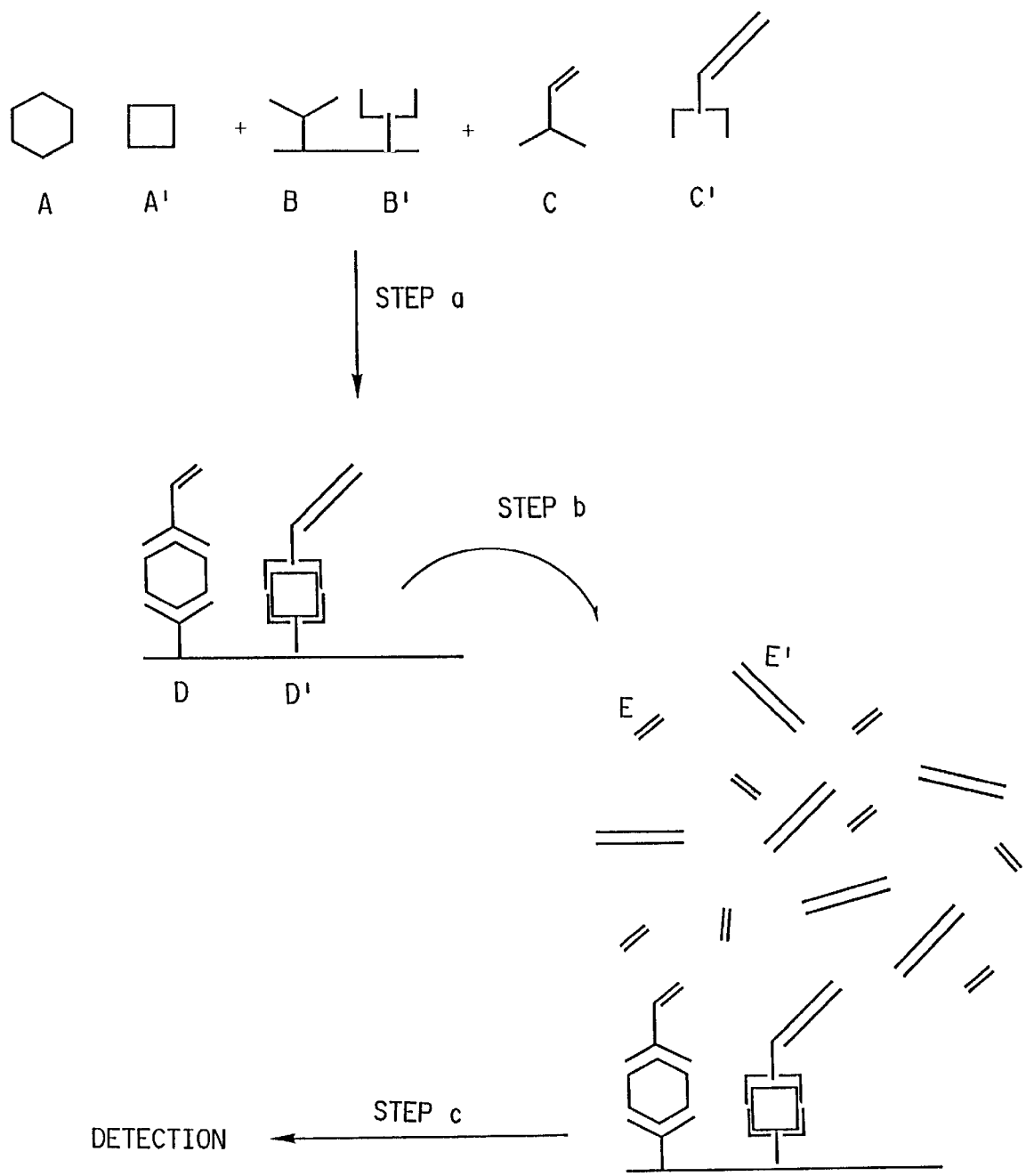
FIG. 4 illustrates the use of the "Direct Target Deposition Method" to detect more than one analyte per sample.

Another embodiment is a variation of the "Direct Target Deposition Method" of FIG. 1, and is illustrated in FIG. 4. The object of this embodiment is to provide a method for detecting several different analytes in a single sample, and may also be referred to as the "multianalyte method".

In FIG. 4, at Step a, the test sample containing different analytes (A and A') is first reacted with the immobilized capture reagents (B and B'), and then with the reporter conjugates (C and C') each comprising a target nucleic acid sequence to form the analyte dependent reporter complexes (D and D') from which excess reagents are removed by washing. In Step b, the ADRCs are contacted with a nucleic acid replication composition and a replication process is performed to produce replicated nucleic acids (E and E'). In Step c, the replicated nucleic acids are detected. In this embodiment, there are more than one reporter conjugates, each comprising an analyte specific antibody or other analyte binding reagent linked to a target nucleic acid sequence. The target nucleic acid sequence for each type of reporter conjugate has a specific length, which is different in length from the target of any other reporter conjugate. Replication of the target nucleic acid sequences thus gives amplification products of different lengths and the presence of different analytes may be conveniently detected by analysis of the amplification products on the basis of size, such as in gel electrophoresis. In a particularly preferred embodiment, the target nucleic acid sequences which differ in length will be designed to comprise the same 5' and 3' primer binding regions, so that the same primers can be used to replicate all of the various targets present in the sample. In another preferred embodiment of multianalyte detection which is useful for detection of multiple sequences in sample nucleic acids (the "multigene assay"), the reporter conjugates will be comprised of target sequences which have been coupled to other nucleic acid sequences which are complementary to specific nucleic acids which may be present in the sample. The complementary sequences will hybridize to sequences present in the sample nucleic acids, thereby immobilizing the reporter conjugates. Target segments of the reporter conjugates will then be replicated, indicating presence of the specific sample sequences.

Figure 6:
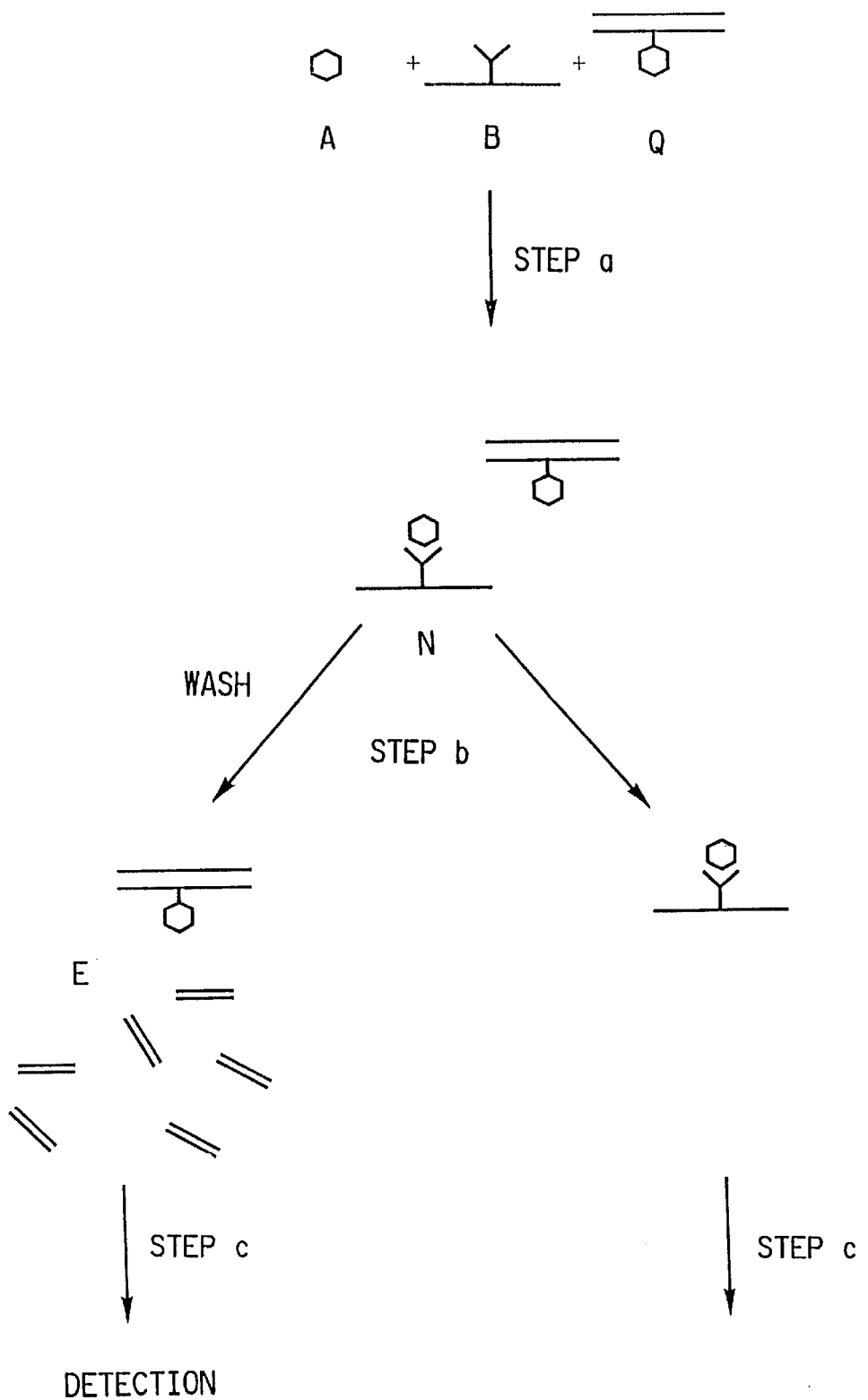
FIG. 6 illustrates the "Competitive Binding Method" of amplifying an analyte-dependent reporter system.

An additional embodiment of the present invention, termed the "Competitive Binding Method", is illustrated in FIG. 6.

In FIG. 6, at Step a of this embodiment, the test sample containing the analyte (A) is first reacted with an immobilized capture reagent (B), such as an antibody, and then with a ligand reporter conjugate (Q) comprising a target nucleic acid sequence bound to a ligand wherein the ligand is capable of competing with the analyte (A) for binding sites on the immobilized capture reagent (B). The reaction results in the formation of an immobilized analyte complex (N) leaving the ligand reporter conjugate (Q) unbound. The ligand reporter conjugate (Q) and the immobilized analyte complex (N) are then separated by washing. In Step b, either the immobilized analyte complex (N) or the ligand reporter conjugate may be contacted with a nucleic acid replication composition. In the case where the ligand reporter conjugate (Q) is contacted, nucleic acid replication occurs and the presences of analyte is detected. In the case where the immobilized analyte complex (N) is contacted, no replication occurs and no replicated nucleic acids (E) are produced. In this embodiment, the ligand reporter conjugate is a conjugate comprising a target nucleic acid sequence and, for example, an antigen or other binding reagent capable of competing with the analyte for binding sites on the capture reagent.

Additionally, one of ordinary skill will recognize that the above several embodiments could be practiced employing alternative immobilization points throughout the assay. For example, in FIG. 6, the ligand reporter conjugate could be immobilized and the capture reagent could be free in solution.

Thus, in all of the above embodiments the production of replicated nucleic acids from a target nucleic acid sequence is used to amplify detection of the analyte.

The process of the present invention may be used to detect the presence of a wide variety of analytes. Generally, these include, but are not limited to, plants, animals, nucleic acid segments, molecules, cells, microorganisms and fragments and products thereof, or any substance for which attachment sites, binding members or receptors (such as antibodies) can be developed. Of particular interest are pathogens, viruses and bacteria. It is contemplated that the sample material will be a liquid, a gas or a solid to be dissolved in, extracted from or suspended in a test fluid. The sample material will most likely be of medical, veterinary, environmental, nutritional or industrial significance. While not attempting to be limiting, it is contemplated that specimens for human, animal, or microbiological sources or habitats may be tested by the present method, including body fluids such as urine, blood, serum, plasma, milk, sputum, fecal matter, lung aspirates, exudates; microbial culture fluids; aerosols; crop materials; soils and ground waters.

The immobilized capture reagent which binds the test analyte will generally be comprised of, for example, a binding protein, lectin, nucleic acid or an antibody, attached to an appropriate support. Any known antibody could serve as the antibody of the immobilized capture reagent. In addition, specific antibodies may be prepared and utilized in this process. In certain instances analyte may be captured directly by nonspecific interaction with the support, as in, for example, the hydrophobic interactions between proteins and polystyrene.

Suitable immobilization supports used in the ADRC, receptor supports and affinity supports (to capture the replicated nucleic acids) include synthetic polymer supports, such as polystyrene, polypropylene, polyglycidylmethacrylate, polystyrene, substituted polystyrene (e.g., aminated or carboxylated polystyrene; polyacrylamides; polyamides; polyvinylchlorides, etc.); glass beads; agarose; or nitrocellulose, etc. These materials may be used as films, wells, beads, particles, pins, pegs or membranes. Alternatively, the supports could comprise magnetic and non-magnetic particles.

These supports can be used to prepare different immobilized reagents. For example, depending on the approach and reagent configuration, separate immobilized support reagents could be prepared for binding the ADRC, for binding of the activated conjugate receptor, or for capture of the products of nucleic acid replication during the detection step. Alternatively, under circumstances in which the analyte, receptor and product binding activities do not compete or interfere with the other binding functions, the analyte, conjugate and product binding reagents could be co-immobilized on the same support. In this way the ADRC, and the receptor support could be prepared and used as separate supports, or the binding reagents could be combined on the same support. Analyte binding molecules, and receptors can be immobilized on the solid support using techniques well known to those skilled in the art. H. Weetall, *Immobilized Enzymes. Antigens, Antibodies and Peptides*, (1975) Marcell Dekker, Inc., New York.

Typically, the immobilized capture reagent can be comprised of glycidyl methacrylate beads of about 30 u in diameter and an antibody such as goat anti-Rabbit IgG antibody. Test beads and antibody are incubated at 4° C. followed by a washing to remove excess antibody. The beads are then treated with bovine serum albumin to bind any unreacted epoxide groups and resuspended in buffer.

In practicing the present invention, two different types of reporter conjugates are contemplated by Applicants. The first type consists of a target nucleic acid sequence coupled to an antibody or other binding member which recognizes an analyte. These can be prepared using variations of methods known to those skilled in the art for linking proteins to amino-oligonucleotides, For example, this may be accomplished using enzymatic tailing methods in which an amino-modified dNTP is added onto the 3' end of the nucleic acid. A. Kumar, *Anal. Biochem.*, 169, 376 (1988). Alternatively, amino-modified bases can be synthetically introduced into the nucleic acid base sequence. P. Li, et al., *Nucleic Acids Res.*, 15, 5275 (1987). Antibodies can then be attached to amino-modified nucleic acids by substituting an antibody for an enzyme in the method of Urdea. M. S, Urdea, *Nucleic Acids Res.*, 16, 4937 (1988).

More specifically, preferred preparation of nucleic acid/antibody conjugates involves the coupling of heterobifunctional cross-linkers to the DNA oligonucleotide targets which in turn are coupled to antibodies using chemistry described by Tseng et. al. in U.S. Ser. No. 07/946247. A key advantage of this linking chemistry over standard protocols in the art is that it reduces the occurrence of unwanted reactions such as homo-DNA or homo-antibody polymers.

To facilitate the chemical attachment of the oligonucleotides to the antibodies, the oligonucleotides are amino-modified by introducing a primary amine group at their 5' end during synthesis using cyanoethyl-phosphoramidite chemistry. The amino-modified oligonucleotides are further modified with a hetero-bifunctional reagent that introduces sulfhydryl groups. The reagent, N-succinimidyl S-acetylthioacetate (SATA) is a heterobifunctional cross-linker agent that uses the primary amine reactive group, N-hydroxyl-succinimide (NHS) to couple to the amino-modified oligonucleotides introducing an acetyl-protected sulfhydryl group. The antibodies are modified with another NHS cross-linking agent, succinimidyl 4-(N-maleimidomethyl) cyclohexane-1-carboxylate (SMCC). The SMCC reacts with primary amine groups within the peptides (e.g., the ε-groups on lysine) of the antibody, introducing a maleimide group (a free sulfhydryl reactive group) to the antibody. The maleimide-modified antibodies are mixed with the SATA modified antibodies. The acetyl-protected sulfhydryl groups on the SATA-modified oligonucleotides are activated with the addition of hydroxylamine to produce reactive, free sulfhydryl groups (U.S. Ser. No. 07/946247). The free sulfhydryl-containing oligonucleotides react immediately with maleimide-modified antibodies forming DNA to antibody conjugates.

The second conjugate type comprises an enzyme coupled to an antibody or other member of a binding pair. These also may be prepared using methods well known to those skilled in the art. D. G. Williams, *J. Immun. Methods*, 79, 261 (1984). Alternatively, enzyme-binding conjugates can be generated using recombinant DNA and genetic engineering techniques. I. Pastan and D. Fitzgerald, *Science*, 254, 1173 (1991). Enzymes suitable for use in a reporter conjugate include, but are not limited to, hydrolases, lyases, oxidoreductases, transferases, isomerases and ligases. Others are peroxidase, glucose oxidase, phosphatase, esterase and glycosidase. Specific examples include alkaline phosphatase, lipases, beta-galactosidase, horseradish peroxidase and porcine liver esterase. The choice of reporter conjugate depends upon which embodiment of the present invention is practiced.

Target Nucleic Acid

Logarithmic nucleic acid replication technology (for example, the polymerase chain reaction (PCR), or the ligase chain reaction (LCR)) provides highly sensitive means for amplifying copies of a specific nucleic acid sequence. These technologies afford two very important capabilities. One is the specificity of the replication process. Information from a single sequence can be specifically replicated in the presence of samples containing complex mixtures of nucleic acids and high concentration of proteins. The second is the high sensitivity afforded by the process. Replications of target DNA on the order of $>10^6$ fold can be achieved by a temperature recycle process. Currently, pathogens can be detected in mixtures of unknown samples by sequence probes; however, the sensitivity approaches approximately only $10^3$ cells/ml. Logarithmic sequence replication of target DNA has now greatly extended probe test sensitivity enabling as few as 1 to 5 cells /100 ml to be detected, A. K. Bej et al., *App. Environ. Microbiol.*, 56, 307 (1990).

As noted above, the target nucleic acid is replicated to produce amplified copies of the target sequence nucleic acids. The design of the target sequence is important because replication requires suitable complementary primer(s); and also because the target can provide for different means of detection and for flexibility in reaction conditions.

Specifically, the target nucleic acid sequence may vary in length from 20 to 5000 bases. Preferably if the target is to be used for PCR amplification it will range between 30 and 1000 bases. If the target is used for LCR amplification the target length will range between 100 and 500 bases. The target may be double-stranded (ds), comprising a hybrid duplex of two complementary nucleic acid strands, or may alternatively, be single-stranded (ss). Double-stranded targets do not require production of a complementary strand to participate in logarithmic chain polymerization. Either or both strands can carry modified bases used for binding or detection. When only one strand of the target is attached to the support, the complementary strand will be free to anneal with primers in the solution phase. Once removed from the support matrix, strand replication is unhindered. Double-stranded targets are thus particularly useful for immobilized targets, since heat denaturation will free one strand which is freed from the support for replication.

Single-strands of double stranded targets however, may also be used when preparing conjugate reagents. For example, as illustrated below, only one strand of the target is used during the first amplification cycle. Annealing and extension of primer #1 can then convert the single-stranded target to a double-stranded duplex. Acting in concert in subsequent cycles, primers #1 and #2 will lead to logarithmic replication of the newly-synthesized double-stranded target nucleic acid. Single-stranded targets offer some reagent preparation advantages in that they are 1) cheaper, since only one strand need be made, and 2) no prior annealing with the complementary strand is required. The same primers may be used for amplification of appropriately designed ss or ds targets.

In a preferred simplification of the Applicants' invention, logarithmic replication can be achieved using a single-stranded target and a single primer. This is achieved by designing the target sequence to contain a primer binding sequence at one end of the ss target and a complement sequence of the primer binding site at the opposite end of the target strand. Annealing and extension of the primer will result in the formation of a complementary target strand containing the identical primer binding sites. In this way both the (+) and (−) strands of the resulting ds target contain an identical primer site at opposite ends of the target duplex, and the same primer used in combination with the polymerase and target nucleic acid promotes replication of both + and − target strands.

The single primer approach affords advantages in reduced assay complexity and increased reproducibility. Simplification is achieved since only one primer must be prepared and provided for detection. More importantly, the single primer can enhance productivity of the nucleic acid acid replication process since each primer has exactly the same melting temperature (Tm). Temperature recycling constraints are thus more easily controlled. Furthermore, the likelihood of nonspecific nucleic acid formation resulting from primer-dimer replication is reduced.

Figure 5:
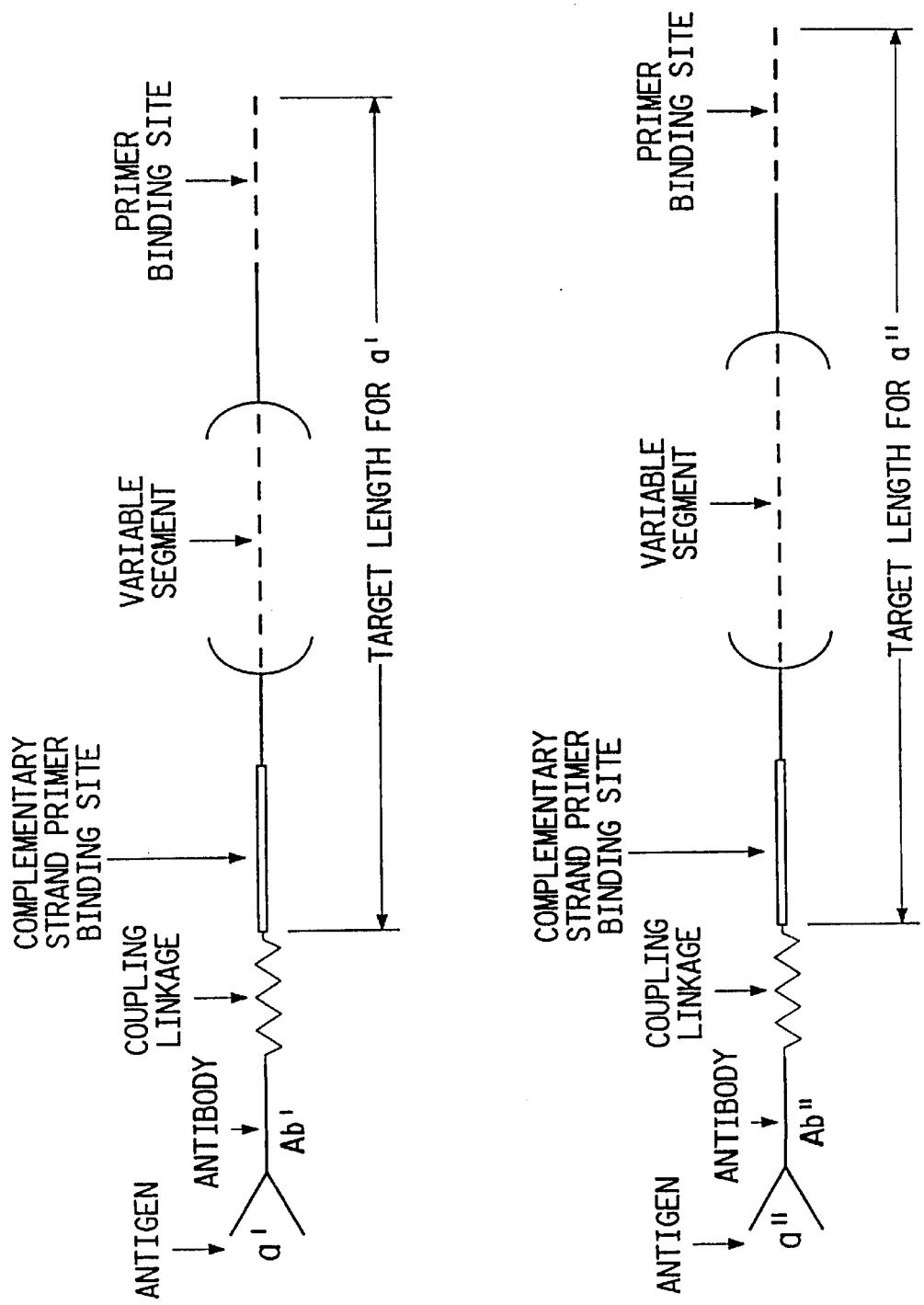
FIG. 5 illustrates a variable length reporter conjugate designed for use in the "Direct Target Deposition Method" to detect more than one analyte per sample.

In other preferred embodiments, the base composition and sequence of the target nucleic acid sequence can be varied to accommodate different assay requirements. For example, the target may contain sequence segments which are not amplified during replication, or variable regions used to alter the length of the target sequence. It is contemplated, for example, that a target nucleic acid sequence may be designed to contain a coupling linkage for the attachment of an antibody or ligand at the 5' end and a primer binding site at the 3' end with a variable region inserted between. The variable region could be of any length or composition, limited only by the requirements of the target amplification method. This is illustrated in FIG. 5, which provides an example of a reporter conjugate wherein the target nucleic acid has been conjugated to an antibody through a chemical coupling linkage at the 5' end. The target oligonucleotide may contain a 5' binding region complementary to one of the replication primers, and a 3' site for binding the other replicated primer. Within the target sequence is a variable region of nucleic acid bases, which could be variable in length or in sequence, thereby providing alternative means of detection of the replicated targets based on size or other factors, such as ability to bind, or ability to emit distinctive signals (such as fluorescence, radioactivity, etc.).

Another preferred embodiment for multi-analyte detection is shown in FIG. 4, wherein target nucleic acids which vary in length are used to detect various analytes. For example, a series of nucleic acid targets having the same primer binding sites and same sequence, but differing only in length of the inner target region could be prepared, and coupled to different binding pairs which are capable of binding to the different analytes (such as analyte-specific antibodies, lectins, receptors, etc.). The replication products of each of these receptor conjugates could then be readily distinguished on the basis of size, and conveniently visualized, for example, by gel electrophoresis. In a "multigene assay", where the analytes to be detected are specific sequences of RNA or DNA contained within sample nucleic acids, the reporter conjugates are comprised of targets of varying lengths coupled to nucleic acid sequences which are complementary to specific portions of the sample nucleic acid. In this way, multiple genes or sequence sites within one sample can be conveniently screened in one assay. The high resolution capability of nucleic acid separation, wherein sequences which vary in length by only one base can be resolved, renders this method extremely attractive when large numbers of samples containing multiple analytes are to be screened.

Additionally, the target sequence can be designed to facilitate detection of the amplified nucleic acids which are capable of emitting detectable signals. For example, the target sequence may provide for incorporation of labeled primers or labeled bases (e.g., fluorescence, radioactive, light emitting) to produce the correspondingly labeled signal generating nucleic acids. The type, number of labeled bases and position within a chain, and between complementary chains, may be designed to facilitate signal detection. In a preferred embodiment, it is desired to position specifically labeled bases in the sequence so as to enable energy transfer between fluorophores, or to enable enzyme channeling between proximally positioned coupled enzymes.

Specifically, energy transfer between suitably labeled bases can be achieved if the distance between the excitation fluorophore (F1) and the emission fluorophore (F2) are within 12 bases (ca. 50A°) in the helical duplex assemblage R. A. Cardullo et al., *Proc. Natl. Acad. Sci. USA*, 85, 8790 (1988). A more preferred distance is between 5 to 12 bases. This can be achieved by designing the target and primer sequences so that one of the labeled bases (F1 and F2) is alternately incorporated in the signal nucleic acid at each turn of the helix. Alternatively, the base sequence of the target or primers can be designed so that F1 and F2 are incorporated into opposite strands of the signal nucleic acid. The position of labeled bases is controlled so that on strand hybridization, F1 and F2 are positioned within the duplex at a distance of <50A°. More preferable, F1 and F2 will be positioned on the same side of duplex one turn apart. Thus, within the signal nucleic acid, both interchain and intrachain labeled bases can position the fluorophores within a distance suitable for energy transfer.

The requirements of fluorophores which participate in energy transfer are well documented. L. E. Morrison, *Anal. Biochem.*, 174, 101 (1988). Generally, to achieve energy transfer it is also important to select the appropriate combination of fluorophores used for labeling the excitation (F1) and emission (F2) bases so that the emission spectrum of the excitation fluorophore (F1) overlaps with the adsorption or excitation spectrum of the excitation fluorophore (F2). For example, the following fluorophore combinations include commonly available suitable candidates for energy transfer:

| Excitation Fluorophore (F1) | Emission Fluorophore (F2) |
| --- | --- |
| Pyrenebutyrate | β-Phycoerythrin |
| Fluorescein | Texas Red |
| Lucifer Yellow | Rhodamine |
| Lucifer Yellow | Texas Red |

-continued

| Excitation Fluorophore (F1) | Emission Fluorophore (F2) |
|---|---|
| Fluorescein | Rhodamine |
| Fluorescamine | Fluorescein |

In another preferred embodiment, the sequences of the target and primers can be designed to incorporate bases labeled with the first member of a binding pair (e.g. digoxigenin, biotin). The incorporated labeled bases can be used to either immobilize the resulting nucleic acids, or to complex them with a second member of the binding pair labeled with a reporter (e.g. streptavidin-alkaline phosphatase, antidigoxigenin-alkaline phosphatase). It is contemplated that the target sequence may be designed to enable the incorporation of different bases or primers; one or more labeled with binding members (e.g., biotin); and one or more labeled with a reporter(s). It is desirable to control the sequence so that the biotin-labeled bases are incorporated predominantly at one end of a chain and the reporter bases incorporated at the other end or some distance from the binding members. Nevertheless, in designing the base sequence it is important to avoid both consecutive runs of C's and G's (3 or more) at the 3' ends, as well as with palindromic sequences. For example, a target gene sequence could contain the following sequence:

```
     1                                           45
5' ATG CGT AGC AGC TTT ACC GCA GAG ATC ATG CCT ATG TAC CAT GCT 3'
3' TAC GCA TCG TCG AAA TGG CGT CTC TAG TAC GGA TAC ATG GTA CGA 5'

46                          75
5' ATC CTA CCT GTA AGT CAT AGC TGT TTC CTG 3' SEQ ID NO:1
3' TAG GAT GGA CAT TCA GTA TCG ACA AAG GAC 5' SEQ ID NO:2
```

The nucleic acid replication substrates are comprised of a target nucleotide sequence, optionally a spacer, and a moiety capable of being activated by an enzyme. The target nucleic acid sequence is prepared according to the guidelines set out above. The moiety capable of activation by an enzyme may be any moiety which forms a reactive intermediate which can bind to a receptor on the solid support of the immobilized capture reagent. In preferred embodiments the enzyme reactive moiety is tyramine.

Reporter conjugates, including the nucleic acid replication substrate and nucleic acid replication conjugate, may contain a molecular spacer segment linking the two functional elements of the conjugate. One purpose of the spacer is to extend the replication segment of the target or binding functions away from the surface of the solid phase support. Useful spacers are well known in the affinity chromatography art. For example, H. Schoot, *Affinity Chromatograph*, (1984), Marcell Deckker, Inc., New York, describes different spacers and their use. Advantageously, the spacer includes a chain of up to about 50 atoms, preferably 5 to 30 atoms. In composition, spacers may be a polyfunctional segment including, but not limited to, one or more of the groups: peptide, hydrocarbon, polyalcohol, polyether, polyamine, polyimine and carbohydrate e.g. -glycyl-glycyl-glycyl- or other oligopeptide, carbonyl dipeptide, and omegaaminoalkane-carbonyl radical such as —NH—$(CH_2)_2$—CO—, a spermine or spermidine radical, omega-alkanediamine radical such as —NH—$(CH_2)_6$—NH— or —HN—$CH_2$—$CH_2$—NH—. The spacer segment may also be comprised of polymeric units such as polysaccharide, polyethylene oxide radicals, glyceryl, pentaerythritol and like radicals. The spacer segment may be linked directly or linked through a divalent heterobifunctional or homobifunctional couplers, for example SATA (N-succinimidyl S-acetylthioacetate), SMCC (succinimidyl 4-(N-maleimidomethyl) cyclohexane-1-carboxylate), p-phenyl diisothiocyanate, dithiobis succinimidyl propionate, 1,4-butanediol diglycidyl ether, a diisocyanate, carbodiimide, glyoxal, glutaraldehyde or sulfosuccinimidyl 6-(4'-azido-2'nitro-phenylamino)-hexanoate.

The length of the target nucleic acid sequences may be extended beyond the sites of primer attachment. The extended length of the target thus can provide an alternative spacers and thus reduce the length or eliminate the need for a molecular spacer, and also perhaps increase the efficiency of target replication. For example, bases added at the target attachment site will extend the target segment away from the point of immobilization. In this way, spacer length can be reduced or in some instances eliminated. Generally, adding 5 to 30 bases to the target will be sufficient to increase the efficiency of immobilized target replication. The composition and length of molecular spacers are designed to prevent interference during amplification of nucleotide target sequence. Recent findings indicate that target sequences next to the aminolink spacer are accessible for primer attachment and logarithmic chain reaction. (S. Stamm and J. Brosius, *Nucleic Acids Research*, 19 1350 (1991).

Once the target nucleic acid sequence is designed, the nucleic acid replication substrates may be prepared using well-established procedures developed for preparation of enzyme-labeled oligonucleotide probes. See e.g., G. H. Keller and Manak, M. M., *DNA Probes*, (1989), pp. 136–148, Stockton Press, New York. More specifically, during the synthesis of the target nucleic acid sequence, a base modified with a spacer arm containing a primary amine can be introduced at either the 5' end or the 3' end of the target. Reagents for introducing a base containing a 5' amino group are commercially available (C8-aminohexyl-ATP and N6-amino-hexyl ATP, Sigma Co)), and methods of accomplishing the introduction into the sequence are known in the art. The N-Monomethoxytrityl-C6-AminoModified cyanoethyl phosphoramidite reagent (Clontech Laboratories Inc., 4030 Fabian Way, Palo Alto, Calif. 94303) or Aminolink™ 2 (Applied Biosystems, Inc.) provide an easy means of introducing a 5' terminal primary aliphatic amine to an oligonucleotide during synthesis of a target oligonucleotide. Detailed procedures for the coupling reaction are available from Clontech bulletin no. PB022789-1, or from Applied Biosystems, Inc., Model 392 Manual. Once the amino-modified nucleic acid target has been prepared, it can then be reacted with succinic anhydride; which extends the length of the side chain and also provides a terminal carboxylic acid which can be activated using standard methods to form the N-hydroxysuccinimide (NHS) intermediate (1). This intermediate can then be chemically coupled to tyramine, for example, to form a nucleic acid replication substrate (2).

(1) NHS(C)n linker-5' target 3'
(2) Tyramine-(C)n linker- 5' target 3'

Generic reagents are also available from Cruachem (460 Spring Park, Herndon, Va. 22070) Clontech Laboratory (4030 Fabian Way, Palo Alto, Calif. 44303) or Applied Biosystems, Inc. (Foster City, Calif.) for introducing internal single or multiple amino groups into the gene sequence. However, end-labeled oligomers tend to be more accessible for binding and reaction than internally labeled nucleic acids.

In another preferred embodiment, it is contemplated that the sequences of the target nucleic acid can be designed to incorporate a ligand. As used herein the term ligand will encompass both ligands which are structurally related to the analyte, and ligands which mimic analyte binding, so long as the ligands have the ability to compete with an analyte for receptor binding sites. Thus, ligand-target conjugates may function as a first member of a binding pair and can mimic the binding properties of an analyte, competing with the binding of an analyte to a second member of a binding pair (e.g., an antibody). For the purposes of the present invention ligands of less than 3000 molecular weight are preferred whereas ligands with molecular weights of less than 1500 are most preferred.

Variability in the positional orientation and number of the incorporated ligands lends flexibility to the target design, allowing for increased assay sensitivity and optimized conjugate interaction with the capture reagents. It is contemplated that ligands can be incorporated into one or both strands of a duplex target nucleic acid. Positionally, ligands can be incorporated either at the 5' or 3' ends of the target or incorporated on internal bases within the nucleic acid sequence, where incorporation at the ends is generally preferred. It is contemplated that any number of ligands may be incorporated per target, however, where the object is to achieve maximum sensitivity of the assay, a relatively small number of ligands is preferred, where a range of one to two is most preferred. In the situation where maximum rate of conjugate capture is desired, a high number of ligands per target is preferred.

The method of incorporation of the ligand into the nucleic acid sequences may be accomplished either by chemical or enzymatic means, or by direct incorporation of ligand labeled bases into the target sequence. Chemical incorporation would utilize chemistry similar to that used for the synthesis of the tyramine replication substrate, as previously discussed. Typically, a base modified with a spacer arm containing a primary amine can be introduced at either the 5' end or the 3' end of the target which can be further modified to a N-hydroxysuccinimide (NHS) intermediate which may in turn be chemically coupled to the ligand.

In a preferred approach, ligand-incorporated sequences are prepared using ligand-labeled bases or primers during polymerase chain reaction. It is contemplated that ligand labeling can be accomplished either through the incorporation of primers modified with ligand(s) or by using ligand-labeled dNTPs. Ligand labeled primers can be prepared using standard oligonucleotide cyanoethyl phosphoramidite chemistry by substituting selected bases with ligand-modified phosphoramidite bases during primer synthesis. Alternatively, if primers are prepared with modified bases containing a linkable molecular spacer, the ligands can be chemically linked to the spacer after primer synthesis. Another method would make use of ligand-labeled dNTPs or amino-modified dNTPs which can be incorporated into a target nucleic acid sequence during the amplification procedure.

There are several advantages to synthesis of ligand-incorporated nucleic acid sequences by PCR as opposed to chemical or enzymatic means. For example, because of failure of sequences inherent in chemical synthesis, targets of longer than 100 bases are more easily constructed. Additionally, where labeled primers are used, it is possible to control both the positioning and number of ligands within one or both strands of the target sequence by the appropriate placement of the ligand in the primers.

In contrast, although the use of labeled dNTPs facilitates the preparation of multivalent ligand reporter conjugates, precise control over ligand number and labeling pattern is less reliable. This is because dNTP-ligand incorporation is dependant on both polymerase discrimination between dNTP and modified dNTP analogs and the frequency of occurrence of a specific base in the target nucleic acid sequence.

It should be appreciated that the above discussion regarding preparation of target nucleic acid sequences and replication conjugates is equally applicable to preparation and design of the reference nucleic acid sequences and reference replication conjugates of the invention.

The binding substrate is comprised of a first member of a binding pair species, optionally a spacer, and a moiety capable of activation by an enzyme. The spacer and moiety are the same as those described for the nucleic acid replication substrate. Members of specific binding pairs suitable for use in practicing the invention can be of the immune or non-immune type. Immune-specific binding pairs are exemplified by antigen/antibody systems or hapten/anti-hapten systems. The antibody member, whether polyclonal, monoclonal or an immunoreactive fragment thereof, of the binding pair can be produced by customary methods familiar to those skilled in the art. The terms immunoreactive antibody fragment or immunoreactive fragment refer to fragments which contain the binding region of the antibody. Such fragments may be Fab-type fragments which are defined as fragments devoid of the Fc portion, e.g., Fab, Fab' and F(ab')$_2$ fragments, or may be "half-molecule" fragments obtained by reductive cleavage of the disulfide bonds connecting the heavy chain components of the intact antibody. If the antigen member of the specific binding pair is not immunogenic e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, Proteins A, G, and immunoglobulins, etc. Also included are non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters and sulfonyl halides, etc. In preferred embodiments, an exemplary binding substrate would be a conjugate of biotin coupled to tyramine via a N-hydroxysuccinimido linker molecule. The binding substrate can be synthesized using well known methods. M. N. Bobrow, et. al., *J. Immunol. Methods,* 125, 279, (1989)

The nucleic acid replication conjugate is comprised of a second member of a binding pair species, optionally a spacer, and a target nucleic acid sequence. The target nucleic acid sequence and the spacer are designed and prepared according to the principles set out above. The second member of the binding pair species is chosen so as to be complementary to the first member of the binding pair species utilized in the binding substrate. As noted above, in a preferred embodiment the binding substrate is a conjugate comprised of biotin, a spacer and tyramine. Thus, the choice of the second member of the binding pair species used in the nucleic acid replication conjugate will be avidin or streptavidin, and thus the binding substrate will comprise avidin or streptavidin as the second member of the binding pair species. The nucleic acid replication conjugates can be prepared using well established procedures. See, e.g., G. H. Keller and Manak, M. M., *DNA Probes*, (1989), pp. 136–148, Stockton Press, New York. More specifically during the synthesis of the target oligonucleotide, a base modified with a spacer arm containing a primary amine could be introduced at either the 5' end or the 3' end. Reagents for introducing a 5' amino group are commercially available (e.g. Aminolink™ 2; Applied Biosystems Inc., 800 Lincoln Centre Drive, Foster City, Calif. 94404). Aminolink™ 2 is added as the last step in the synthesis of the oligomer. The amino-modified nucleic acid target is then activated by a bifunctional ester to both extend the length of the side chain and to provide a terminal carboxylic acid which can then be activated using standard methods to form N-hydroxysuccinimide (NHS) intermediate (1). This intermediate can then be chemically coupled with avidin to form the nucleic acid replicating conjugate (3):

(1)     NHS(C)n     linker-5'xxxxxxxxxxxxxxxxxxxxxxxxxxxxxx 3'
(3)    Avidin   -(C)n.    linker-5'xxxxxxxxxxxxxxxxxxxxxxxxxxxxxx 3'

Generic reagents are also available from Cruachem, and Clontech for introducing internal single or multiple amino groups into the target nucleic acid sequence. However, end labeled oligomers tend to be more accessible for binding and reaction than internally labeled nucleic acids.

Primers

In current practice, replication of the target nucleic acid sequence requires "primer" oligonucleotides which, as used herein, refers to all oligonucleotides which anneal to target sequences to facilitate replication of the target.

When target replication is performed by polymerase chain reaction two specific primers are used. Each primer specifically hybridizes with one of the two complementary strands of the target (or if the target is single-stranded (ss) one of the primers is specific for the second strand after synthesis). Replication of the target requires that the 5' end of the primer which is complementary to the (−) sense target strand (primer #2), corresponds to a region of the (+) sense strand which is 5' to the 3' end of the (+) sense strand specific primer (#1). Additionally, the primers should not contain regions with sufficient complementarity to form primer-dimers. Within these constraints, the total length of the primers may range from shorter than, to longer than, the target. In general, primers 10–30 bases in length are most practical.

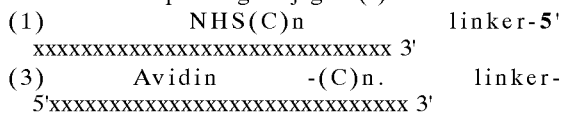

Primers may also contain sequences at their 5' ends that have no complement in the target (5' overhang or 5' mismatch).

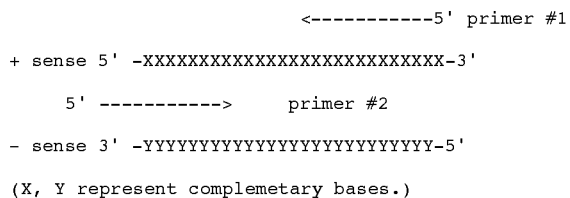

(X, Y represent complemetary bases.)

This 5' overhang or 5' mismatch can be used to incorporate functionalized bases (e.g., signal-generating or binding member-derivatized bases) on the primers, or to extend the length of the replicated nucleic acid products by adding extra sequences. These additions can be useful for capture of the resulting nucleic acids and/or signal detection. In the primer a 3' segment complementary to the target can be joined to a variety of different 5' segments. Thus, a series of primers with a fixed hybridizing region linked to different signal generating tails can be made. The signal generated would depend on the 5' region of the primer(s) used and could be tailored to the detection method of interest. Hence, a single target sequence can be used with different primers containing varying 51 overhangs or mismatches to generate a number of different sequence specific responses.

Typically, in PCR-type amplification techniques the primers have different sequences and are not complementary to each other. Depending on the desired test conditions, the sequences of the primers should be designed to provide for both efficient and faithful replication of the target nucleic acid. Some simple rules are useful in selection and design of the primers. Typically, primers should be 10 to 35 base pairs in length having a 50 to 60%, G+C composition. The calculated Tm's for a given primer pair should be balanced. For this purpose, a 2° C. for A or T and 4° C. for G or C can be added together to estimate the Tm of the oligonucleotide. (Thein and Wallace, "The use of oligonucleotide as specific hybridization probes in the Diagnosis of Genetic Disorderst",in *Human Genetic Diseases: A Practical Approach*, K. E. Davis Ed., (1986) pp. 33–50 IRL Press, Herndon, Va.). Depending on the selected conditions, Tm's between 55° C. and 80° C. are suitable. In addition to the Tm's, the complementarity at the 3' end of the primers is an important consideration. Generally, complementarity of primer pairs should be avoided, especially at the 3' ends. Also, consecutive runs of C's and G's (3 or more) at the 3' ends of the primers along with palindromic sequences should be avoided. Consideration should also be given to the concentration of primer molecules in the replication milieu. Primer concentrations between 0.01 and 1.0 uM are generally suitable, with concentrations of about 0.05 to 1.0 uM being optimal.

When the ligase chain reaction (LCR) is used for replication of a target double-stranded nucleic acid, two sets of target-specific primers will be required. The members of one set of primers are complementary to adjacent sequences found on a given strand of the target, while the members of the second set are complementary to adjacent sequences on the opposite strand. In this way a set of adjacent primers is specific for each target strand. During the replication process the target nucleic acid is heated to denature the two target strands. The four complementary oligonucleotide primers comprising the two primer sets are then hydridized near their melting temperature to the separated target strands. A thermal-stable ligase will covalently attach the adjacent primers on each target strand. Only adjacent primers that are perfectly complementary to the target will be ligated together. In this way, the products from the first stage of ligation become targets for the next round of ligation. The products thus increase exponentially with continued cycles of target denaturation, primer hydridization and ligation steps.

The requirements for non-complementarity between primers, size, base composition and melting temperature requirements of the primers tend to be similar to those stated above for PCR replication. Generally, primers for LCR replication should be sufficiently long so that each will preferentially bind to its specific binding site on the target nucleic acid. To insure specificity of ligation, reactions can be carried out near the melting temperature (Tm) of the oligonucleotide primers. At higher temperatures single-base mismatch at the junction can form. This results not only in an imperfect double helix but destabilizes hydridization of the mismatched oligonucleotides.

In either PCR or LCR type replications, the primers may contain bases labeled with reporter(s) or labeled with one member of a specific binding pair. For example, biotin and fluorescein residues may be incorporated into the primer during CE phosphoramidite synthesis (NEN Products, Du Pont, Boston, Mass.; or Clontech). Incorporation of the primers during amplification will also result in nucleic acid products containing biotin and fluorescein. In this way, primer incorporation during replication process can be used as a preferred means of introducing reporters and affinity labels in the replicated nucleic acids.

Assay conditions

Practicing the analyte-dependent reporter system of the present invention requires several steps. First, an analyte-dependent reporter complex (ADRC) is formed. This is accomplished using well-known immunoassay reagents and techniques. The reagents can be configured for sequential, competitive, sandwich, and immunometric immunoassay approaches. Harlow, E. and Lane, D. L., *Antibodies—A Laboratory Manual*, (1988), pp. 555–612, Cold Spring Harbor Lab., Cold Spring Harbor, N.Y.

Once the ADRC complex has been formed excess free reagents is removed. This is an important step since any free reagent and non-specifically bound reporter can contribute to the replication process. To aid in reducing non-specific binding, stringent wash conditions which do not cause dissociation of the ADRC, such as used in nucleic acid hybridization tests, can be employed since target replication and readout are based on nucleic acid chemistry. For example, heating, pH changes, or (and) the addition of formamide, detergents and salts can be used to increase the efficiency of the wash step. Too stringent conditions can lead to dissociation of the ADRC or destruction of the immunoassay reporter. Tolerance to stringent wash conditions will vary with the nature of the analyte, binding member and specific reporter used. The stringent conditions must, therefore, be experimentally optimized for each assay. However, in washing to reduce non-specific binding, if some of the ADRC is lost, this can be compensated for by additional target replication realized by increasing the number of temperature recycle steps.

In cases where the ADRC is sensitive to stringent wash conditions, a catalyzed reporter assay (FIG. 2) can be used. In this configuration reaction of the ADRC with the substrate results in covalent coupling between the target nucleic acid and the support. After coupling, the solid support is washed leaving the covalently bound target nucleic acid complex. Specifically, a tyramine target substrate could be used with an HRP enzyme reporter to covalently couple the target to the support. In this way, enzyme amplifications could be accomplished and stringent wash conditions used before target replication.

In the next step, the target nucleic acid sequence is replicated. If PCR is the replication method used, the target sequence is mixed with the nucleic acid replication composition (100 ul) comprising two primers (100 pmol/primer), a thermally stable DNA polymerase such as Taq DNA polymerase (2 units), required nucleotides (dNTP 200 uM/base) which may be signal generating or ligand-containing nucleic acids, Tween 20 detergent (0.05%), 20 mM TRIS/HCl buffer (pH 8.3), $MgCl_2$ (1.5 mM), KCl (25 mM), and nuclease-free gelatin (100 ug/ml).

Generally, excess $Mg^{++}$ in the replication reagent composition can result in the non-specific amplification whereas insufficient $Mg^{++}$ will reduce yields. It is known that deoxynucleotide triphosphates (dNTP) bind $Mg^{++}$, and the amount of binding depends upon the dNTP concentration. In a reaction composition containing all four bases (dNTP) this leaves a final free $Mg^{++}$ concentration of ca. 0.7 mM of the original 1.5 mM $Mg^{++}$. If the dNTP concentrations are changed significantly, a compensatory change in $MgCl_2$ may be necessary.

Because of the diversity of applications in which the present invention can be used, adjustments in the concentrations and reagent compositions of the nucleic acid replication reagent composition may be required. Practical guidelines for optimizing and adjusting the replication milieu can be found R. K. Saiki and Gelfand, D. H., in *PCR Technology*, (1989), pp. 7–22, Stockton Press, New York.

The reaction mixture is covered with mineral oil to prevent evaporation. The target nucleic acid is then denatured to separate the duplex nucleic acid strands. Generally this is carried out a high temperature (90–95° C.) for 15 seconds; however, a longer initial time can be required to assure complete denaturation. Annealing of the oligonucleotide primers to the target nucleic acid template is usually accomplished by lowering the temperature to 37 to 60° C. for 30–60 seconds. Polymerase extension of the primers can then be accomplished by equilibration at 72° C. for 10 to 60 seconds, depending on the length of the signal-generation products. The denaturation, primer annealing and primer extension steps are repetitively carried out in sequence to amplify the strand number of the signal-generation product. The temperature cycling is typically performed 10 to 40 times depending on the desired degree of replication. The reaction can then be stopped by addition of EDTA (10 mM) and chilling to 4° C.

In general, if LCR is the replication protocol used, the target sequence of the ADRC is mixed with two sets of adjacent oligonucleotides (40 fmol each); each set will be complementary to one of the complementary target nucleic acid strands; in 10 ul of buffer containing 20 mM Tris.HCl buffer pH 7.6, 100 mM KCl, 1 mM EDTA, 10 mM NAD, 10 mM dithiothreitol, 4 ug salmon sperm DNA and 15 nick-closing units of a thermostable ligase, for example, *T. aquatics* ligase, (Tabor, S. and Richardson, D. C. (1985) Proc. Natl. Acad. Sci. USA 82, 1074–1078).

The reaction mixture is then protected from evaporation, for example, by covering with a drop of mineral oil, and then heated to 94° C. to insure separation of the target strands. Annealing of the oligonucleotide primers to the target is usually accomplished by lowering the temperature to between 37 to 60 degrees. An optimum temperature close to melting temperature of the primers is usually selected, but must be determined dependent upon the primer length and composition of the specific primers. The melting and primer annealing cycle are then repeated 10 to 30 times. The reaction is then chilled to 4° C. to stop the reaction.

The next step involves detection or visualization of the amplified nucleic acids. This can be accomplished by several means including (a) direct detection of the duplex nucleic acids using intercalating dyes; (b) indirect or direct detection of ligands, isotopes or reporters incorporated in the nucleic acids; (c) hybridization of reporter probes to the amplified nucleic acids; or (d) direct detection of replicated product following separation of replicated product from reaction milieu based on increased size of replication product.

Specifically, amplified nucleic acids can be detected in the reaction mixture by adding intercalating dyes. Of particular use are those dyes of the ethidium, phenazines, furocomarins, phenothiasines and quinoline type which on intercalation with the duplex strands of nucleic acids change dye detection properties. General reviews and further information can be obtained in Berman et al., *Ann. Rev. Biophys. Bioeng.*, 20, 87 (1981). For example, a preferred dye is ethidium bromide which on nucleic acid intercalation can be detected by excitation of the reaction mixture with short-wave uv light (259 nm).

Incorporation of modified free bases or modified primers during nucleic acid replication provides a means of introducing bases modified with ligands, isotopes, or reporters. If ligase-type replication is used, oligonucleotides with modified bases already incorporated could be used to replicate the target sequences. These techniques afford several detection strategies. For example, the incorporation of biotinylated or ligand modified bases provides means of isolating the amplified nucleic acid products from solution onto a solid support and discarding the unincorporated bases. The addition of an avidin-signal-generating corrugate there facilitates detection. The amplified sequences may also contain signal-generating labeled bases. These can be detected directly on the solid phase support. Alternatively, methods of collecting and detecting biotinylated DNA fragments on magnetic beads containing immobilized avidin or streptavidan are described by J. Wahlberg et al., Mol. Cell Probes, 4 285 (1990).

In another alternative, the sequence of the amplified segment could be designed to position fluorescent bases within the signal nucleic acids for energy transfer or position the biotinylated bases so that binding of avidin-labeled enzyme(s) reporters would result in enzyme channeling. Using these approaches the amplified target can be detected without the need for separation from the unincorporated bases. According to molecular modeling and recent reports, R. A. Cardullo et. al., Proc. Natl. Acad. Sci. USA, 85, 8790 (1988), energy transfer can be achieved at distances between the fluorophores of as much as 12 bases apart. However, optimum distance appears to be somewhere between 5 to 12 bases. At one fluorophore base per helix turn, this positions the donor and acceptor fluorophores in appropriate proximity for energy transfer.

Analyte Quantitation

The analyte-dependent reporter system (ADRS) response depends upon the quantity of analyte present in the sample, and also upon the efficiency of sequence amplification. While analyte concentrations in samples can be interpolated from standard curves by experimentally relating assay response under fixed reaction conditions and known analyte concentrations, the efficiency of sequence replication is difficult to predict and control because of procedural and reaction variables. Furthermore, amplification is highly sensitive. Hence, if false negative test response can be identified, the absence of analyte can be more reliably determined and the useful range of the assay extended.

Applicants contemplate that at least two types of internal controls can be used to compensate for changes in the efficiency of sequence replication and to provide means of identifying false negative test response. Applicants refer to these as "amplification, or replication control", and "capture control". An "amplification control" refers to a nucleic acid sequence called the "reference sequence" (specifically, a different sequence than the target sequence nucleic acid) and its corresponding cognate primer(s). In use, the reference sequence and cognate primers could be included in the nucleic acid replication reagent composition, and would serve to demonstrate that reaction conditions are permissive for sequence amplification. During testing if the amplification control yields a signal, but the target sequence does not, then the lack of target sequence amplification cannot be the result of test conditions non-permissive for amplification and the result indicates an analyte concentration below the detectable level.

The amplification control can also serve as the internal reference for analyte quantification. For this application, the reference sequence is added at a known concentration approximating the analyte concentration to be detected. During the replication reaction, the reference sequence will theoretically be amplified with the same efficiency as the target sequence. By determining the ratio of the signal responses from the reference sequence and the target sequence, the concentration of the analyte may be determined. In this approach standard curves are determined by measuring the ratio of the responses resulting from the target sequence and the reference sequence in samples containing a range of known analyte concentrations and a fixed concentration of reference sequence. In this way, variations in efficiency of nucleic acid replication can be compensated. Assay response can thus be more accurately related to analyte concentration.

The reference sequence must be similar in molecular weight to the amplification sequence, but must be capable of producing a separate and distinct "replicated reference nucleic acid" which is detectably distinguishable from the replicated target sequence nucleic acid. This can be achieved by designing target and reference sequences to contain unique bases. In this way during replication, a unique base or primer labeled with ligands, reporters, isotopes or reactive groups can be incorporated respectively into the nucleic acid products of both the reference sequence nucleic acids and target sequence nucleic acids. The resulting nucleic acids are thus labeled with separate reporters, or can be isolated for detection via hybridization reactions or binding with complementary members of a specific ligand binding pair.

A "capture control" comprises an analyte reference sequence conjugate (properly configured for each embodiment—see below) and cognate primer(s). The capture control sequence conjugate would be included during the analyte capture step of the assay; and the cognate primer pair would be included in the nucleic acid replication composition. In this configuration, a failure to detect the capture control replications could result from either a lack of capture or conditions non-permissive for amplification. By using different sequences for the capture and amplification controls, both controls can be included in each reaction chamber allowing differentiation between failed capture and failed replication reaction conditions. Inclusion of these controls is possible only because each of the three amplification sites, (target sequence, amplification control and capture control) could be designed to generate a sequence-specific, differentially detectable signal.

dNTP and primer levels should be adjusted so that each of the three replication reactions can proceed to completion. Targets and cognate primers should have similar Tm, length and other characteristics that effect amplification efficiency.

EXAMPLES

The following examples are meant to illustrate key embodiments of the invention but should not be construed to be limiting in any way.

Preparation of Reagents

Oligonucleotides to be used as the reporter or as primers are prepared using standard cyanoethyl (CE) phosphoramidite coupling chemistry on controlled pore glass (CPG) supports in an automated DNA oligonucleotide synthesizer (Generator™, Du Pont Co., Wilmington, Del., and Model 392, Applied Biosystems, Inc., Foster City, Calif.) (Beaucage and Caruthers, Tetrahedron Lett., 22 (20), 1859 (1981); Caruthers et al, Genetic Engineering, vol. 4, ed., (1982); Stelow and Hollaender, Plenum Publishing Corp., New York). The amino-modifying phosphoramidite reagent Aminolink 2™ is obtained from Applied Biosystems, Inc., Foster City, Calif. Oligonucleotides are radio-labeled with [$\alpha^{32}$P] cordycepin 5'-triphosphate and scintillation fluid (Biofluor™) for scintillation counting is obtained from NEN Products, Du Pont Co., Boston, Mass. and scintillation counting is accomplished using a Beckman Model LS3801 scintillation counter (Beckman Instruments, Inc., Palo Alto, Calif.). Deoxynucleotydyl transferase is obtained from Promega, Inc., Madison, Wis. Poly-tergent SLF-18 is obtained from Olin Corp., Stamford, Conn. Kodak Xomat™AR 2 X-ray film for autoradiography is obtained from Eastman Kodak Co., Rochester, N.Y. The reagents, SATA (N-succinimidyl S-acetylthioacetate) and SMCC (succinimidyl 4-(N-maleimidomethyl) cyclohexane-1-carboxylate) are obtained from Pierce, Rockford, Ill. The SATA and SMCC coupling chemistry is described by Tseng et al., in commonly owned U.S. Ser. No. 07/946247. Reporter antibody, used in the reporter conjugate (AffiniPure Goat anti-Rabbit IgG, H+L) is obtained from Jackson ImmunoResearch Labs., Inc.; Product No.:111-005-045. Antibody reaction components are separated from the oligonucleotide components by high-pressure liquid chromatography (HPLC) using a Zorbax 250 Gel Exclusion column (9.4×250 mm, with 0.2M sodium phosphate buffer pH 7.0 and a column flow rate of 1 ml/min.) (MacMod Analytical Inc. Chadds Ford, Pa.) connected to a Waters 600 E System controller and a Waters 991 Photodiode Array detector (Millipore Corp., Milford, Mass.). Injections were made with a Waters 700 Satellite WISP—automated injection system. Test beads of glycidyl methacrylate, (oxirane acrylic beads) functioning as the immobilized capture are purchased from Sigma (Product No. O-9754, Sigma Chemical Co., St. Louis, Mo.). Densitometers used in the following examples were either a Densigraph 100™ (Graphic Technology Inc., Cherry Hill, N.J.) or the Model RD107R Quanta Log Densitometer (MacBeth Corp., Newbough, N.Y.). Basic polymerase chain reaction (PCR) protocols are described in Saiki, R. S. Scharf, F. Faloona, K. Mullis, G. Horn, H. A. Erlich, and N. Amheim, 1985. Science 230:1350 and the amplification reaction is done using reagents obtained in the Perkin Elmer-Cetus GeneAmp® kit (N801-0055), the Perkin Elmer-Cetus 9600 GeneAmp® PCR System thermalcycler (Perkin Elmer-Cetus, Norwalk, Conn.). PCR protocols used in the present invention were modified to amplify short (<150 bases) single-stranded DNA target sequences. In all of the examples provided below, the ADRS assay is demonstrated using polymerase chain reaction (PCR) replication techniques, however it should be understood that any suitable method of nucleic acid replication may be used including Ligase Chain reaction, and isothermal or autocatalytic methods.

Example 1

Amplified Analyte Detection In A Mouse IgG Assay Using Direct Target Deposition Method Oligonucleotide Preparation While not intending to be limiting, and for illustration only, the sequences and primers used in replication could be synthesized with the following sequences.

```
Target Sequence for Single Primer Amplification:

1                                                      45
5'  ATG CGT AGC AGC TTT ACC GCA GAG ATC ATG CCT ATG TAC CAT GCT 3'
3'  TAC GCA TCG TCG AAA TGG CGT CTC TAG TAC GGA TAC ATG GTA CGA 5'

46                            75
5'  ATC CTA CCT GTA AGT AAA GCT GCT ACG CAT 3'  SEQ ID NO:3
3'  TAG GAT GGA CAT TCA TTT CGA CGA TGC GTA 5'  SEQ ID NO:4

Target/Primer Binding Sites for Single Primer
Amplification:

1                                                      45
5'  ATG CGT AGC AGC TTT ACC GCA GAG ATC ATG CCT ATG TAC CAT GCT 3'
3'  TAC GCA TCG TCG AAA TGG CGT CTC TAG TAC GGA TAC ATG GTA CGA 5'
5'  ATG CGT AGC AGC TTT AC  3' Primer 1 SEQ ID NO:5

3' CA TTT CGA CGA TGC GTA 5'  SEQ ID NO:5
     46                            75
5'  ATC CTA CCT GTA AGT AAA GCT GCT ACG CAT 3'  SEQ ID NO:3
3'  TAG GAT GGA CAT TCA TTT CGA CGA TGC GTA 5'  SEQ ID NO:4

Target Sequence for Double Primer Amplification:

5'  ATG CGT AGC AGC TTT ACC GCA GAG ATC ATG CCT ATG TAC CAT GCT 3'
3'  TAC GCA TCG TCG AAA TGG CGT CTC TAG TAC GGA TAC ATG GTA CGA 5'

5'  ATC CTA CCT GTA AGT CAT AGC TGT TTC CTG 3'  SEQ ID NO:1
3'  TAG GAT GGA CAT TCA GTA TCG ACA AAG GAC 5'  SEQ ID NO:2

Primer 1:

5' ATG CGT AGC AGC TTT AC 3'  SEQ ID NO:5

Primer 2

3' CAG TAT CGA CAA AGG AC 5'  SEQ ID NO:6

Target Sequence/Primer Binding Sites for Double Primer
Amplification:

5'  ATG CGT AGC AGC TTT ACC GCA GAG ATC ATG CCT ATG TAC CAT GCT 3'
3'  TAC GCA TCG TCG AAA TGG CGT CTC TAG TAC GGA TAC ATG GTA CGA 5'
5'  ATG CGT AGC AGC TTT AC  3'  Primer 1 SEQ ID NO:5

3' CA GTA TCG ACA AAG GAC 5' Primer 2 SEQ ID NO:6
5'  ATC CTA CCT GTA AGT CAT AGC TGT TTC CTG 3'  SEQ ID NO:1
3'  TAG GAT GGA CAT TCA GTA TCG ACA AAG GAC 5'  SEQ ID NO:2
```

Many alternative base sequences and chain lengths can also be employed within the guidelines discussed herein.

Nucleic Acid Replication Composition

The replication composition useful in amplifying the sequence target in polymerase-type amplifications may comprise a solution containing replication buffer (25 mM KCl, 20 mM TRIS hydrochloride [pH 8.13], 1.5 mM $MgCl_2$, 0.05% Tween 20 and 0.1 mg/ml autoclaved gelatine [wt/vol]), 200 mM each of the dNTPs, 1.0 uM of each primer, 2.5 U of Taq DNA polymerase made up in double-distilled water containing (0.1% wt/vol.) diethylpyrocarbonate. When nucleic acid replication is carried out using labeled deoxynucleotide triphosphates, the above replication composition may be modified so that one or more of the deoxynucleotide triphosphates (dNTPs) is replaced with labeled bases. Biotinylated dUTP (bio-dUTP) (Enzo Biochem, New York, N.Y.) and fluorescein labeled dCTP (F-dCTP) (Boehringer Mannheim Biochemicals, Indianapolis, Ind.) can be obtained from Bethesda Research Laboratories, Inc., Maryland, and may be substituted respectively for dTTP and dCTP in a 1:3 molar ratio of labeled to unlabeled base. Generally, a 20 to 30% incorporation of labeled bases is preferable in order to maintain efficient hybridization V. T. Chan et al., *Nucleic Acids Res.*, 13, 8083 (1985).

Nucleic Acid Amplification

Target and reference sequence replication may be performed using a DNA Thermal Cycler and Gene Amp Kit using native Taq polymerase (Perkin-Elmer Cetus Corp., Norwalk, Conn.).

For amplification, 50 to 100 ul of the above replication composition could be added to ADRC test well containing the immobilized target sequence. The replication composition is agitated to assure contact with the support, and then overlaid with 75 ul of mineral oil (BDH Paraffin oil). The nucleic acid sequences are then denatured at 94° C. for 1 to 3 min. A total of 25 to 10 temperature recycles could be performed under the following conditions: denaturation at 94° C. for 0.5 to 1 min., primer annealing at 37 to 60° C. for 0.5 to 1 min., DNA extension at 72° C. for 1 to 2 min.

Preparation of N-Hydroxysuccinimide-Activated Target Nucleic Acid

Preparation of a 5' activated spacer arm can be accomplished by substituting thymidine bases in the target sequence with C5 thymidine analogs substituted with a C12 spacer linker arm terminating in an active esters as described by J. Ruth et al., *Fed. Proc.*, 44 (5), 1622 (1985). The C5 amino-modified thymidine analog can be synthetically incorporated into the oligonucleotide sequence using conventional phosphoramidite activation chemistry (Applied Biosystems, Foster City, Calif., Model 392 DNA synthesizer) and then derivatized with DSS (disuccinimidyl suberate) Pierce, Rockford, Ill., as described by Ruth et al., (1985) to form an active N-hyroxysuccinimide (NHS) ester.

Preparation of Antibody/Nucleic Acid Reporter Conjugate

A solution of the NHS oligonucleotide (0.5 umole equivalents) may be coupled with 0.25 umoles of goat anti-mouse IgG (Fab fragment specific) antibody (ICN) in a 1M $NaHCO_3$ buffer at pH 9.0. The reaction mixture is then incubated for 2 hr at room temperature in the dark. The antibody reporter conjugate is purified away from free nucleic acid and antibody using polyacrylamide (4 to 7%) gel electrophoresis under non-denaturing conditions (TBE) buffer). The conjugate is recovered by cutting out the conjugate band and placing it into a stoppered Econo-column (Bio-Rad) containing phosphate buffer saline solution (pH 7.4) as described by G. H. Keller and Manak, M. M., in DNA Probes, (1989), pp. 129–142, Stockton Press New York. The conjugate is then concentrated by centrifugation using a prewashed Centricon 10 (Amicon) microconcentrator.

Polystyrene beads (approximately 1–4$\mu$ microsphere beads, PolySciences, Inc., Warrington, Pa.) are coated with goat anti-mouse IgG (Fc fragment specific) antibody (Sigma Chemical, St. Louis, Mo.) in 0.1 carbonate buffer pH 9.6 to prepare the solid phase antibody supports. After incubating overnight at 4° C. the antibody solution is removed by centrifugation and aspiration. The beads are blocked with a solution of 2% bovine serum albumin (BSA) dissolved in the above carbonate buffer. The beads are then washed free of excess reagents by rinsing three times with a 10 mM phosphate buffered (pH 7.4) saline solution with 0.05% Tween (PBST) and then resuspended in PBST. Dilutions of mouse IgG (mIgG) are made by dilution into PBST solution containing 1% BSA (BSA-PBST). Aliquots of mouse IgG solution are added to tubes containing the microsphere beads, to yield a range of mouse IgG concentrations from 0, 0.001, 0.01, 0.1, 1.0 to 10 ng/tube of mIgG. A solution (5 ul) containing 0.01 ug/ml of the antibody/target reporter conjugate described previously is then added, and the assay mixture is incubated for 1 hour. Excess reagent is then removed by washing the microbeads with three exchanges of PBST wash fluid.

Target replication is then achieved by adding 100 ul of the nucleic acid replication composition to test microsphere beads. The test solutions are mixed to assure contact with the support and then overlaid with 50 ul of mineral oil (BDH Parrafin oil). The target sequence is then denatured at 94° C. for 1 to 3 min. The reaction mixtures are thermally cycled using a DNA Thermal Cycler (Perkin-Elmer Cetus Corp., Norwalk, Conn.) according to manufacturer instructions.

Measurement of test response in target sequence-amplified wells could be achieved following equilibration with the above sequence amplification composition modified to contain biotinylated dATP and fluorescein labeled dCTP as described above.

For detection of the amplified signal-generating nucleic acids, the amplification reaction fluid in each well is removed and transferred to microtiter plate wells coated with streptavidin as follows: Polystyrene EIA Microtiter Strips (NUNC) are filled with streptavidin (Sigma, St. Louis, Mo.) solution prepared in 0.1M carbonate buffer pH 9.6. After incubating overnight at room temperature (RT) the solution can be removed and the strips blocked with a solution of 2% bovine serum albumin (BSA) dissolved in the above carbonate buffer. The strips can then be washed free of excess reagents by rinsing three times with PBST. The test fluids are then incubated in the avidin coated wells for 30 min. and then washed free of unbound target. The wells are then filled with 10 mM phosphate buffer (pH 7.4) saline (PBS) buffer, and the fluorescence in each well is measured.

Assay response in this example would result from binding of the antibody reporter conjugate to the surface of the test wells. The target sequence contained on the reporter conjugate is replicated using replication composition containing biotinylated bases and bases labeled with a fluorophore as previously described. The incorporation of these bases during sequence replication results in the formation of nucleic acids containing both biotinylated and fluorescent bases. For detection, the nucleic acids would be isolated by capture onto an avidin solid-phase support, and could then be detected by measuring the signal nucleic acid fluorescence. Assay intensity would increase in proportion to the concentration of mouse IgG analyte in the sample.

Example 2

Amplified Analyte Detection In A Mouse TgG Assay Using The Indirect Target Deposition Method Preparation of Tyramine Nucleic Acid Substrate A solution of the NHS target oligonucleotide (0.5 umole equivalents) can be coupled with 0.5 umoles tyramine (recrystallized from water, Aldrich, Milwaukee, Wis.) in 2.5 ml of dimethylformamide by addition of 1.0 ml of 1M triethylammonium bicarbonate, pH 7.5 and then heated at 50° C. for 3 hours. The solution can then be concentrated to dryness on a rotary evaporator and purified by recrystallization from water or by HPLC using a reverse-phase column in a Perkin-Elmer high performance liquid chromatograph.

Preparation of Streptavidin Nucleic Acid Conjugate

A solution of the NHS oligonucleotide (0.5 umole equivalents) could be coupled with 0.25 mmoles of streptavidin (Sigma) in a 1M $NaHCO_3$ buffer at pH 9.0. The reaction mixture can be incubated for 2 hr at room temperature in the dark. The conjugate can be purified away from free sequence and avidin using polyacrylamide gel eleclrophoresis under non-denaturing conditions using a TBE buffer as described by M. S. Ureda, *Methods in Enzymol.*, 146, 22 (1987) and M. S. Ureda et al., *Nucleic Acids Res.*, 16, 4937 (1988).

Polystyrene microsphere beads (approximately 1–4$\mu$) are coated with goat anti-mouse IgG (Fc fragment specific) antibody in 0.1M carbonate buffer pH 9.6. After incubating overnight at room temperature the antibody solution is removed by centrifugation and aspiration. The microbeads are blocked with a solution of 2% bovine serum albumin (BSA) dissolved in the above carbonate buffer. The beads are then washed free of excess reagents by rinsing three times with PBST. Antigen dilutions of mouse IgG are prepared in PBST containing 1% BSA (BSA-PBST) as described in Example 1, and are then added to two sets of tubes containing the beads. The beads are incubated at 37° C. for 1 hour, followed by washing with PBST. Goat anti-mouse IgG-HRP (Boehringer Mannheim) is diluted, as recommended by the manufacturer, and incubated for 1 hour at 37° C. Excess reagent is then removed by washing and aspirating three times with PBST.

A stock solution of biotin-tyramine conjugate (1 mg/ml) in dimethyl sulfoxide is then prepared as described above. Just before use, the stock solution is diluted in 0.1M borate buffer pH 8.5 containing 0.01% $H_2O_2$ to prepare a substrate solution containing 10 ug/ml biotin-tyramine. The substrate solution is then added to both sets of the test beads and incubated for 15 minutes at room temperature. Unreacted substrate is then removed and the test beads washed with PBST at 37° C.

For a comparison of detection sensitivity, streptavidin-alkaline phosphatase (Sigma Co., St. Louis, Mo.) is diluted as recommended by the manufacturer and added to one set of test beads as a reference control. For target nucleic acid replication, streptavidin-target sequence conjugate (1 ug/ml) in PBST is added to the second set of beads. Both sets of test beads are then incubated at room temperature for 30 minutes and then washed 3 times with PBST to remove unreacted conjugate.

Measurement of response in reference control wells is then achieved by addition of p-nitrophenyl phosphate solution (1 mg/ml) in 10 mM diethanolamine (pH 9.5), 0.5 mM $MgCl_2$ buffer to both sets of test beads. After 15 minutes at 37° C., color development is stopped by addition of 50 ul of 0.1M EDTA and optical densities are read at 405 nm in a microtiter plate reader (Molecular Devices Corp., California).

Measurement of test response in target nucleic acid amplified wells is achieved by first equilibrating the second set of beads with the replication composition as described in Example 1 above. The test mixtures are agitated to assure contact with the bead supports and then overlaid with 75 ul of mineral oil (BDH Paraffin oil). The target sequence is denatured at 95° C. for 1 to 3 min. The reaction mixtures are thermally recycled 30 times using a DNA Thermal Cycler according to manufacturer instructions. For detection of the amplified target nucleic acids, 1 ul of a stock solution of 100 ml of ethidum bromide (0.5 mg/ml) in a Tris Acetate EDTA buffer (pH 8.1) containing 40 mM Tris base, 2 mM acetic acid, 0.2 mM EDTA is added to the reaction supernatant. The solution is then excited with shortwave light at 254 nm and the fluorescence is detected.

Assay response in this example would result from the ADRC-HRP catalyzed deposition of biotin/tyramine reporter on the test bead surface followed by subsequent binding of the streptavidin signal-generating sequence target. The target is then amplified using nucleic acid replication composition as described in Example 1 and the resulting nucleic acid products are detected by dye intercalation. Assay intensity would increase in proportion to the concentration of mouse IgG in samples, and could be detected at mIgG concentration below that which is detectable using an non-amplified ADRC-AP reporter.

Example 3

Amplified Analyte Detection In A Mouse IgG Assay Using Catalyzed Direct Target Deposition Method Polystyrene microspheres (1–4$\mu$) are coated with goat anti-mouse IgG (Fc fragment specific) antibody in 0.1M carbonate buffer pH 9.6. After incubating overnight at room temperature (RT) the antibody solution is removed and the strips blocked with a solution of 2% bovine serum albumin (BSA) dissolved in the above carbonate buffer. The beads are then washed free of excess reagents by rinsing three times with a 10 mM phosphate buffered (pH 7.4) saline solution containing 0.05% Tween 20 (PBST). Antigen dilutions of mouse IgG (mIgG) dissolved in a solution PBST containing 1% BSA (BSA-PBST) are then added to the beads as described in Example 1. The beads are then incubated at 37° C. for 1 hour followed by washing 3 times with PBST, and treated with goat anti-mouse IgG-HRP as described in Example 2.

For catalyzed reporter deposition, a stock solution of tyramine-gene target substrate (1 mg/ml) in dimethyl sulfoxide is prepared. Just before use, the stock solution is diluted in 0.1M borate buffer pH 8.5 containing 0.01% $H_2O_2$ to prepare a substrate solution containing tyramine-sequence target substrate (10 ug/ml). The substrate solutions is then added to the test beads and incubated for 30 minutes at room temperature. The reaction mixture is then removed and the test wells washed with PBST at 37° C.

Measurement of test response in sequence amplified wells is achieved following equilibration of each set of test beads with the above sequence replication composition modified to contain biotinylated and fluorescein labeled nucleotides as described in Example 1 above. The test solutions are mixed to assure contact with the support and then overlaid with 75 ul of mineral oil (BDH Paraffin oil). The target sequence is then denatured at 95° C. for 1 to 3 minutes, and then the reaction mixtures are thermally recycled 30 times using a DNA Thermal Cycler according to the manufacturer instructions.

For detection of the amplified signal-generating nucleic acids, the replication reaction fluid in each set of test beads well is removed and transferred to microtiter plate wells coated with streptavidin as follows: Polystyrene EIA microtiter plate wells are filled with streptavidin (Sigma) solution prepared in 0.1M carbonate buffer pH 9.6. After incubating overnight at room temperature (RT) the streptavidin solution is removed from each well and microtiter wells blocked with a solution of 2% bovine serum albumin (BSA) dissolved in the above carbonate buffer. The wells are then washed free of excess reagents by rinsing three times with a 10 mM phosphate buffered (pH 7.4) saline solution containing 0.05% Tween 20 (PBST). Once prepared the above test fluids are then transferred and then incubated in the avidin-coated wells for 30 minutes and then washed free of unbound target replication reagents. The wells are then filled with PBS buffer, and the fluorescence in each well is measured.

Assay response in this example would result from the ADRC-HRP catalyzed deposition of tyramine-sequence target reporter on the test bead surface. The immobilized target nucleic acid is then amplified using sequence replication composition containing biotinylated bases and bases labeled with a fluorophore. The incorporation of these bases during sequence replication would result in nucleic acids containing both biotin and fluorescent-labeled bases. For detection, the nucleic acids are isolated by capturing on an avidin solid-phase support and then detected by measuring the nucleic acid fluorescence. Fluorescent intensity increases with the concentration of mouse IgG analyte in the sample.

Example 4

Detection and Quantitation of Mouse IgG Using A Reference Internal Control Assay Preparation of biotin, isotope and fluorescence-labeled bases The target or reference sequences, and primer sequences can be designed to enable incorporation of biotin, isotope or (and) fluorescence labeled bases or primers. In this way, the sequence replication process can produce nucleic acid strands providing means of both capture and detection. For example, either the target nucleic acid or a reference sequence could be prepared with the following bases:

```
Reference Nucleic Acid/Primer Binding Sites:

1                                              45
5' ATG CGT AGC AGC TTT ACC GCA GAG ATC ATG CCT ATG TAC CAT GCT 3'
3' TAC GCA TCG TCG AAA TGG CGT CTC TAG TAC GGA TAC ATG GTA CGA 5'
5' ATG CGT AGC AGC TTT AC 3' Primer 1 SEQ ID NO:5

3' AT CAT CTT TGT CGA CTG 5' Primer 5 SEQ ID NO:13
       46                                             75
5' ATC CTA CCT GTA ATA GTA GAA ACA GCT GAC 3' SEQ ID NO:7
3' TAG GAT GGA CAT TAT CAT CTT TGT CGA CTG 5' SEQ ID NO:8

Primer 1 (capture):

5' biotin-ATG CGT AGC AGC TTT AC 3' SEQ ID NO:5

Primer 5 (reporter):

3' AT CAT CTT TGT CGA CTG-Fluorophore (Flu) 5' SEQ ID NO:13

Target Sequence/Primer Binding Sites:

5' ATG CGT AGC AGC TTT ACC GCA GAG AT-
C ATG CCT ATG TAC CAT GCT 3'
                                         3'
TAC GCA TCG TCG AAA TGG CGT CTC TAG TAC GGA TAC ATG GTA CGA 5'
biotin-ATG CGT AGC AGC TTT AC 3' SEQ ID NO:5

3' AT CAT CTT TGT CGA CTG-Flu 5' SEQ ID NO:13
             5' ATC CTA CCT GTA ATA GTA GAA ACA GCT GAC 3' SEQ ID NO:7
             3' TAG GAT GGA CAT TAT CAT CTT TGT CGA CTG 5' SEQ ID NO:8
```

Alternatively, sequences could be designed so that the positions of fluorescent-labeled bases are in appropriate spatial alignment for efficient energy transfer between fluorophores.

Polystyrene microsphere beads (1–4μ diameter) are coated with goat anti-mouse IgG (Fc fragment specific) antibody (ICN) in 0.1 carbonate buffer pH 9.6. After incubating overnight at room temperature the IgG solution is removed and the beads blocked with a solution of 2% bovine serum albumin (BSA) dissolved in the above carbonate buffer. The beads are then washed free of excess reagents by rinsing three times with 10 mM PBST. For calibration, a standard curve is established by determining the assay response from a series of samples containing known concentrations of mouse IgG (mIgG). To prepare the standard solutions, dilutions of mIgG are made by dissolving mIgG in PBST solution containing 1% BSA (BSA-PBST). Each standard is added to the same quantity of test beads. In this way, samples containing a range of mouse IgG concentrations from 0, 0.001, 0.01, 0.1, 1.0 to 10 ng/tube of mIgG may be prepared. A test sample containing an unknown concentration of mIgG is also added to a separate set of beads.

The tubes containing both the test and standard beads are then incubated with 10 ul of a solution (0.1 ug/ml) of the above anti-mIgG antibody/target reporter conjugate. Excess reagents are then removed by washing with PBST.

Amplification of the target nucleic acid on both the antibody target reporter conjugate and a reference sequence is achieved by adding to test wells 100 ul of a replication composition which also contains replication control at appropriate sequence and primer concentrations. The test solutions are mixed to assure contact with the support and then overlaid with 50 ul of mineral oil (BDH Parrafin oil). The target and reference sequences can then be denatured at 94° C. for 1 to 3 minutes, and the reaction mixtures are thermally recycled 30 times using a DNA Thermal Cycler according to manufacturer instructions as described in Example 1 above.

In this example, the capture primer #1 for both the target and reference nucleic acid are identical, and prepared so as to contain biotinylated dUTP at the 5' end of the primer strand. The reporter primers (#2) for the two different targets will comprise different sequences, one specific for the target nucleic acid, and one specific for the reference nucleic acid. Each primer sequence is complementary for the antisense stand and its respective target. Both the reporter primer and reference primer can be amino-modified at their 5' end with amino-modifying phosphoramidite reagent during their synthesis on an automated DNA synthesizer. The amino-modified reporter primer can be reacted with a fluorescein NHS ester, labeling the 5' end of the primer with fluorescein. The amino-modified reference primer can be labeled with a rhodamine fluorophore NHS ester using the same chemistry.

For detection of the amplified nucleic acids, the amplification reaction fluid in each test well is removed and transferred to microtiter plate wells previously coated with streptavidin as follows: Polystyrene EIA Microtiter Strips (NUNC) are filled with streptavidin (Sigma, St. Louis, Mo.) solution prepared in 0.1M carbonate buffer pH 9.6. After incubating overnight at room temperature the streptavidin solutions are removed and strips blocked with a solution of 2% bovine serum albumin (BSA) dissolved in the above carbonate buffer. The strips can then be washed free of excess reagents by rinsing three times with a 10 mM phosphate buffered (pH 7.4) saline solution containing 0.05% Tween 20 (PBST). The test fluids resulting from the above nucleic acid replications are then incubated in the streptavidin coated wells for 60 minutes and then washed free of unbound signal nucleic acid products and reagents. The rhodamine and fluorescein fluorescence in each well is measured for both the standards and the test sample, and the ratio of rhodamine to fluorescein fluorescence in the standard samples and test samples is computed. The fluorescein response in the test sample would then be corrected based upon the average rhodamine to fluorescein response determined in the standard samples. The corrected fluorescein response would then be used to determine the mIgG concentration by interpolation of fluorescein response measured in the mIgG standard wells. Fluorescein intensity in test samples would increase in proportion to the concentration of mouse IgG analyte in the sample.

Example 5

Preparation of a 75 base Oligonucleotide Reporter-Antibody Conjugate Using Heterobifunctional Crosslinking Chemistry, for use in the Direct Target Deposition Method Oligonucleotide Synthesis or Preparations The 75 base oligonucleotide used as a nucleic acid reporter (target) was amino-modified at the 5' end, that is, a primary amine group was introduced at the 5' end of the oligonucleotide target. The primary amine group was later used in the NHS-heterobifunctional chemistry to couple the DNA target to the test antibody(Ab). Amino-modification was accomplished using the CE phosphoramidite chemistry during the synthesis of the target on the automated DNA synthesizer (Smith, L. M., S. Fung, M. W. Hunkapiller and L. E. Hood (1985) Nucleic Acids Res. 11:2399–2412; Sproat, B. S., B. Beijer and P. Rider (1987) Nucleic Acids Res. 15:6181–6196). Aminolink 2™ (Applied Biosystems) an amino-modifying phosphoramidite reagent was incorporated during the last phosphoramidite coupling cycle of the oligonucleotide synthesis.

The following target primer sequences were designed and synthesized to be used as the target sequence in the conjugate reporter.

```
Target Sequence (75mer) for Double Primer Conjugate
Reporter system:

5'X-GGC AGG AAG ACA AAC ACT GGC TGG TCT GTG GTG CTG TGC TTG TTC CCC TGT
  ..CCT AGT ATT GTT TTC TGG GTT GGT 3' SEQ ID NO:9

(X = Aminolink 2™ amino-modifer)

Primer 3 (3' primer for the 75mer) (17mer) sequence:

5'ACC AAC CCA GAA AAC AA 3' SEQ ID NO:10

The primer binding site for Primer 3 (3' primer for the
75mer) is illustrated below:

5'X-GGC AGG AAG ACA AAC ACT GGC TGG TCT GTG GTG CTG TGC TTG TTC CCC TGT
  ..CCT AGT ATT GTT TTC TGG GTT GGT 3' SEQ ID NO:9
       3'AA CAA AAG ACC CAA CCA 5' SEQ ID NO:10
```

The underlined sequence is the complementary sequence of the Primer 3 or the "3' primer binding site".

The double stranded 75mer reporter produced from primer extension (replication) is illustrated below:

```
5'X-GGC AGG AAG ACA AAC ACT GGC TGG TCT GTG GTG CTG TGC TTG TTC CCC TGT
3'  CCG TCC TTC TGT TTG TGA CCG ACC AGA CAC CAC GAC ACG AAC AAG GGG ACA

..CCT AGT ATT GTT TTC TGG GTT GGT 3' SEQ ID NO:9
  ..GGA TCA TAA CAA AAG ACC CAA CCA 5' SEQ ID NO:11

Primer 4 (5' primer of the 75mer) (16mer) primer binding
site is illustrated below:

5'X-GGC AGG AAG ACA AAC ACT GGC TGG TCT GTG GTG CTG TGC TTG TTC CCC TGT
3'  CCG TCC TTC TGT TTG TGA CCG ACC AGA CAC CAC GAC ACG AAC AAG GGG ACA
5'  GGC AGG AAG ACA AAC A 3' SEQ ID NO:12

..CCT AGT ATT GTT TTC TGG GTT GGT 3' SEQ ID NO:9
..GGA TCA TAA CAA AAG ACC CAA CCA 5' SEQ ID NO:11
```

The underlined sequence is the complementary sequence of Primer 4 or the "5' primer binding site".

The crude target and primer oligonucleotides were analyzed for full length products and failure sequences by 8% polyacrylamide/8.3M urea gel (denaturing) electrophoresis (Sanger, F and A. R. Coulson. 1978. FEBS Lett. 87:107) and standard autoradiography. The oligonucleotides were radiolabeled at the 3' end with [$\alpha^{32}$P] cordycepin 5'-triphosphate (5000 Ci/mmol) using terminal deoxynucleotydyl transferase (TdT). This was accomplished by adding 100 ng of the oligonucleotide to 10 ul reaction solution containing 100 mM cacodylate, pH 6.8, 1 mM $CoCl_2$, 0.1 mM DTT, 100 μg/ml BSA and 10 units of TdT. The reaction was incubated at 37° C. for 30 min. An aliquot, 2 ul, of the labeled oligonucleotides was added to 6 ul of a loading solution (90% formamide, 0.05% bromophenol blue and 0.05% xylene cyanol FF), mixed, heated (90° C. for 1 min.) and loaded on an 8% polyacrylamide/8.3M urea gel (40×30× 0.04 cm) in 1× TBE buffer (8.9 mM Tris-borate, pH 8.2, 2 mM EDTA). The electrophoresis was carried out by applying 55 Watts (or 1.35 W/cm) to the gel for 2.5 hrs or until the bromophenol blue ran to the bottom of the gel. The gel was transferred onto a piece of Whatman 3 MM paper (Whatman International, Ltd., Maidstone, England) and dried on a Model 583 gel dryer (Bio-Rad Laboratories, Richmond, Calif.) at 80° C. for 1 hr. The dried gel and X-ray film (Kodak Xomat™AR 2) were placed in an X-ray cassette containing an intensifying screen (Du Pont Cronex® Lighting Plus™, Du Pont Co., Wilmington, Del.), and the film was exposed for an appropriate amount of time to obtain an autoradiographic image.

Synthesis of the Reporter Conjugate

The rationale or the strategy used for synthesizing the reporter conjugate is the same as outlined in the specification. The protocol involves first coupling a sulfhydryl group to the 75-base amino-modified oligonucleotide using the SATA reagent followed by the addition of a maleimide group to the goat antibody using the SMCC reagent, and finally the linking of the 75-base, SATA-modified oligonucleotide to the maleimide-modified goat antibody.

Coupling a Sulfhydryl Group to the 75-base, Amino-modified Oligonucleotide

The 75-base amino-modified oligonucleotide, 1.4 mg (60 nmoles), was added to a 667 uL reaction mixture containing 100 mM sodium bicarbonate buffer, pH 9.0, 13.3 mg SATA (N-succinimidyl S-acetylthioacetate) 50% dimethyl formamide(DMF). The SATA reagent was prepared by dissolving 20 mg in 500 uL of DMF. The reaction mixture was allowed to proceed for 30 min. at 25° C., then immediately applied to a Sephadex® G-25 (Pharmacia LKB, Uppsala, Sweden) column, 1×20 cm and eluted at room temperature with 100 mM sodium phosphate buffer pH 6.5 at a flow rate of 1 ml/min. Fractions were monitored by absorbance at 280 nm (Pharmacia LKB #2138 Unvicord S Monitor) and collected on a Pharmacia Model Frac 100 fraction collector. The first peak fractions (1.0 ml), containing the SATA-modified oligonucleotides were pooled and concentrated to ~1.0 ml using an Amicon Centricon™ 3 concentrator (Amicon, W. R. Grace & Co., Danvers, Mass.). The Centricon™ 3s were placed in a SM24 rotor (Du Pont Sorvall, Newtown, Conn.) and spun in a Du Pont Sorval® RC5B Refrigerated Superspeed centrifuge, @ 7500 rpm (7000×g) for 45 min. at 20° C. The samples were pooled, placed in another set of Centricon™ 3s and spun again for 45 min. using the same centrifuge protocol. The SATA-modified oligonucleotide concentrate (~1.0 ml) was recovered using the protocol recommended by the manufacturer (Amicon), and was saved at 20° C. in the dark until needed for the final DNA-Ab coupling protocol.

Coupling Maleimide Groups to the Goat Antibody

The reporter antibody, used in the reporter conjugate (AffiniPure Goat anti-Rabbit IgG, H+L, 1.5 mg/ml), 3 mg, was added to a 2.7 ml reaction mixture containing 100 mM sodium phosphate buffer, pH 7.0, 2 mg SMCC, 1.5% dimethyl formamide(DMF). The SMCC was prepared by dissolving 5 mg in 84 uL of DMF (60 mg/ml). This reaction was started 75 min. after the 75 base amino-modified oligonucleotide was reacted with the SATA reagent. The reaction mixture was allowed to proceed for 30 min. at 25° C., then immediately applied to a Sephadex® G-25 column, 1×20 cm and eluted at room temperature with 100 mM sodium phosphate buffer pH 6.5 at a flow rate of 1 ml/min. Fractions were monitored by absorbance at 280 nm and collected on a Pharmacia Model Frac 100 fraction collector. The first peak fractions (1.0 ml), containing the SMCC-modified (maleimide-modified) goat antibody were pooled (4 to 6 ml) into one tube. The reaction product was ready for coupling to the SATA-modified oligonucleotides.

Coupling the SATA-modified Oligonucleotides to the Goat Maleimide-modified Antibodies The pooled maleimide-modified goat antibody fractions (5 ml) were added to a 15 ml Falcon® 2059 tube (Becton and Dickinson and Co., Lincoln Park, N.J.). The concentrated 75 base SATA-modified oligonucleotide (~1.0 ml) was added to the same reaction tube and mixed well with the maleimide-modified goat antibody. The coupling reaction was initiated by adding 75 ul of 1M hydroxylamine (HA)

(Pierce, Rockford, Ill.), pH 7.0, 50 mM EDTA and mixing well. The reaction was transferred to an Amicon Model 3' MiniCell (6 ml stirred cell) concentrator fitted with a YM5 filter (Amicon). The MiniCell was connected to a helium source, adjusted to 60 psi, and placed on a magnetic stirrer. The reaction was allowed to proceed while the reactions major components (modified-Abs, modified-oligonucleotides and newly formed DNA/Ab conjugate) were being concentrated at room temperature covered with aluminum foil. The reaction volume was reduced to approximately 1.0 ml (60 min.). The reaction was removed from the MiniCell and transferred to a Wheaton 224812, amber 4.0 ml vial (Wheaton, Millville, N.J.) and incubated at room temperature on a Lab Quake™ (Labindustries, Inc., Berkeley, Calif.), rotating until the total reaction time reached 2 hrs. The reaction was terminated by the addition of 10 ul of 10 mM N-ethylmaleimide in DMF.

Isolation of the Oligonucleotide-Antibody Conjugates from the Modified Oligonucleotide Component The 75-base-oligonucleotide-goat-antibody conjugate (the reporter conjugate or the oligonucleotide-antibody conjugate) and the antibody reaction components were separated from the oligonucleotide components by high-pressure liquid chromatography(HPLC). This was achieved using a Zorbax 250 Gel Exclusion column (9.4×250 mm, with 0.2M sodium phosphate buffer pH 7.0 and a column flow rate of 1 ml/min.) connected to a Waters 600 E System controller and a Waters 991 Photodiode Array detector. Injections (200 ul) were made with a Waters 700 Satellite WISP—automated injection system. The first peak fractions (0.5 ml) resulted in a mixture of the oligonucleotide-antibody conjugate and the maleimide modified-antibody reaction component.

The fractions were further analyzed for the oligonucleotide-antibody conjugate by gel electro-phoresis and standard autoradiography. The conjugate-linked oligonucleotide was radio-labeled at the 3' end with $[\alpha^{32}P]$ cordycepin 5'-triphosphate (5000 Ci/mmol) using TdT. This was accomplished by adding 2 ul of the HPLC-isolated fraction to a 10 ul reaction solution containing 100 mM cacodylate, pH 6.8, 1 mM $CoCl_2$, 0.1 mM DTT, 100 µg/ml BSA, 10 units of TdT and 1 µCi of $[\alpha^{32}P]$ cordycepin 5'-triphosphate. The reaction was incubated at 37° C. for 30 min. The samples were then analyzed on a standard sodium dodecyl sulfate-polyacrylamide gel electrophoresis (SDS-PAGE; Laemmli, U.K. 1970 Nature 227:680–685) and standard DNA denaturing (urea) polyacrylamide gels (Sanger, F and A. R. Coulson,1978, FEBS Lett. 87:107).

An aliquot, 4 ul, of the labeled products was added to 12 ul of protein gel loading buffer (62.5 mM Tris, pH 6.8, 2% SDS, 10% glycerol, 0.01% bromophenol blue). The samples were loaded on a SDS-PAGE protein gel (8% polyacrylamide separation gel (15×15×0.075 cm), 375 mM Tris, pH 8.8, 0.5% SDS; 4% polyacrylamide stacking gel, 0.12M Tris, pH 6.8, 1% SDS; in Laemmli running buffer, 0.25 mM Tris.HCl,192 mM glycine, 0.1% SDS, pH 8.3). The electrophoresis was started at 100 V (6.7 V/cm.) and was increased to 225 V (15 V/cm.) after the sample moved through the stacking gel. The electrophoresis was continued until the dye front had migrated approximately 13–14 cm.

A second aliquot of 2 ul was added to 6 ul of a loading solution (90% formamide, 0.05% bromophenol blue and 0.05% xylene cyanol FF), mixed, and loaded on a 8% polyacrylamide/8.3M urea gel (40×30×0.04 cm) in 1× TBE buffer (8.9 mM Tris-borate, pH 8.2, 2 mM EDTA). The gel electrophoresis was carried out by applying 55 Watts (or 1.35 W/cm) to the gel until the bromophenol blue ran to the bottom of the gel.

For autoradiography, both the SDS-PAGE protein gel and the DNA denaturing PAGE gel were transferred onto a piece of Whatman 3MM paper and dried on a Bio-Rad Model 583 gel dryer at 80° C. for 1 hr. The dried gel and X-ray film (Kodak Xomat™AR 2) were placed in an X-ray cassette containing an intensifying screen (Du-Pont Cronex® Lighting Plus™), and the film was exposed for an appropriate amount of time to obtain an autoradiographic image.

The spectrophotometric scans of the HPLC fraction and data obtained from the autoradiography procedures described above were used to determine which HPLC fractions contained the oligonucleotide-antibody conjugate free of the 75-base SATA-modified oligonucleotide precursor. The peak fractions were pooled and stored at 4° C.

Example 6

Amplification of a Rabbit IgG Assay using the Direct Target Deposition Method

Preparation of Immobilized Capture Reagent for Immunoassays

The immobilized capture reagent (test beads) were prepared by adding 100 mg of glycidyl methacrylate beads (oxirane acrylic beads 30µ), to a 500 ul solution of the capture antibody, goat anti-Rabbit IgG antibody (0.5 mg) (AffiniPure Goat anti-Rabbit IgG, H+L, 1.5 mg/ml) in PBS buffer. The test beads were incubated with rotation for 20 hrs. at 4° C. The excess goat antibody was removed by centrifugation and aspiration. The test beads were then pretreated with bovine serum albumin (BSA) to pacify the unreacted epoxide groups. The test beads were incubated with a 1 mg/ml solution of BSA in PBS (10 mM phosphate buffered (pH 7.4) saline solution) buffer for 2 hr at room temperature. The test beads were washed with water to remove the BSA, then washed 4× with PBS buffer, and finally resuspended in 1.0 ml of PBS buffer (0.1 mg/gL) containing 0.02% azide.

The Immobilized Capture Reagent's Immuno-Reactivity and Immunoassay Procedure

The test beads' immuno-reactivity is assayed in two replicates by adding 0.5 mg of the test beads to 250 ul Tris sample buffer (TSB) (50 mM Tris.HCl, 75 mM sodium chloride, 0.1% poly-tergent SLF-18, 0.1% BSA and 0.02% azide) in 500 ul "eppendorf" tubes (Eppendorf®, Brinkmann Instruments Co., Westbury, N.Y.). To assay tubes receiving the test antigen, Rabbit IgG (Purified Rabbit IgG), 20 ul of the stock solution (100 µg/ml) was added and the solutions were incubated at room temperature for 30 min. To the control assay tubes (test beads with no added antigen), 20 ul of TSB buffer was added and the solutions were incubated at room temperature for 30 min. The test beads were pelletted by centrifugation and the supernatants were removed by aspiration. Each test was washed 3× with TSB buffer. Each test was then incubated at room temperature with 50 ul of the goat anti-R-IgG- alkaline phosphatase conjugate (Sigma product No., A-8025) stock solution in a final reaction volume of 250 ul for 1 hr. The conjugate reagent was removed by centrifugation and aspiration and, then each test was washed 4× with TSB buffer. The BCIP (bromochloroindoyl phosphate: Sigma product No.710-3) reagent (20 ul) was then added to each tube and incubated at room temperature for 30 min. The color (blue-green) developed in the test was read to determine the degree of immuno-activity.

Determination of the Reporter Conjugate's Immuno-Activity and the Immunoassay's Signal to Noise Response The oligonucleotide-antibody conjugate (75 base target oligonucleotide conjugated to the goat anti-R-IgG) was radio-labeled at the 3' end with [$\alpha^{32}$P] cordycepin 5'-triphosphate (5000 Ci/mmol) using TdT. This was accomplished by adding 10 ul of the pooled HPLC peak fractions of the oligonucleotide-antibody conjugate to 20 ul reaction solution containing 100 mM cacodylate, pH 6.8, 1 mM $CoCl_2$, 0.1 mM DTT, 100 μg/ml BSA, 30 units of TdT and 20 μCi of [$\alpha^{32}$P] cordycepin 5'-triphosphate. The reaction was incubated at 37° C. for 30 min. Ten microliters of the labeled oligonucleotide-antibody conjugate was added to 50 ul of "cold" conjugate. Serial dilutions from 5 ul down to 0.005 ul of the oligonucleotide-antibody conjugate were assayed for immuno-reactivity. For each dilution to be tested, two test replicates were set up by adding 0.5 mg of the test beads to 250 ul TSB buffer in 500 ul "eppendorf" tubes. To assay tubes receiving the test antigen, Rabbit IgG (Purified Rabbit IgG: Sigma, N I-5006), 20 ul of the stock solution (100 μg/ml were added and the solutions were incubated at room temperature for 30 min. Two control assay tests (test beads with no added antigen) were made for each conjugate dilution. To each control test, 20 ul of TSB buffer were added and the solutions were incubated at room temperature for 30 min. The test beads were pelletted by centrifugation and the supernatants were removed by aspiration. Each test was washed 3x with TSB buffer. Next, each test was incubated at room temperature for 1 hr in 250 ul TSB buffer and the appropriate dilution of the [$^{32}$P] labeled oligonucleotide-antibody conjugate. The non-reacted, labeled reporter conjugate reagent was removed by centrifugation and aspiration, and then each test was washed 4x with TSB buffer. Each tube of assay test beads or assay control beads was resuspended in 10 ul of TSB buffer and transferred to a scintillation vial containing 10 ml of scintillation fluid (Biofluor™) The amount of radio-label in each test was counted in a Beckman Model LS3801 scintillation counter (Beckman). The amount of signal and non-specific label for each dilution was graphically plotted. These data were used to determine a dilution of the 75 base oligonucleotide-goat Ab conjugate at which the non-specific reactivity was indistinguishable from background. This dilution and the immediate dilutions below this dilution of the reporter conjugate were used in immunoassays followed.

Dose-Response Immunoassay using the Reporter Conjugate

Aliquots made from serial dilutions of the test analyte stock solution, rabbit IgG (100 μg/ml) (Sigma, N I-5006), 1 ug, 1 ng and 1 pg, were added to 500 ul tubes containing 0.5 mg of test beads in 250 ul TSB. There was also a control assay tube containing 250 ul of TSB buffer, 0.5 mg test beads and no rabbit IgG. The assay solutions were incubated at room temperature (antigen capture step) for 30 min. The test beads were pelletted by centrifugation and the supernatants were removed by aspiration. Each test was washed 3x with TSB buffer, and then incubated at room temperature with 250 ul equivalent dilution of the TSB containing 0.02 ul of the oligonucleotide-antibody conjugate for 30 min. The supernatants were removed by centrifugation and aspiration. The test beads were washed 4x with TSB and then 1x with water. The beads were resuspended in 50 ul of water.

Target Sequence (Oligonucleotide) Amplification Procedure

Amplification of the 75-base-oligonucleotide target sequence conjugated to the reporter antibody (goat anti-rabbit IgG, Jackson ImmunoResearch Labs.) was performed using the polymerase chain reaction (PCR). The protocol required two separate additions of primers. The first addition was made before the initial cycle; the 3' primer was added at a 10x excess over the 5' primer. A second addition of primers was made after the fifteenth replication cycle with both primers added at the same concentration. The amplification reaction was done using reagents cited above and the following conditions. For each test sample, a final reaction volume of 50 ul (containing 10 mM Tris*HCl, pH 8.3, 50 mM KCl, 1.5 mM $MgCl_2$, 0.001% gelatin, 100 μM dATP, 100 μM dCTP, 100 μM dGTP, 100 μM dTTP and 0.25 units Taq DNA polymerase) was prepared. For the initial reaction, 2.5 ul of the 3' primer (400 nM stock sol.) and 2.5 ul of the 5' primer (40 nM stock sol.) were added to a MicroAmp™ reaction tube (Perkin Elmer-Cetus) containing 25 ul of distilled water. Five microliters of the test beads resuspended in water were added to the primers and the tube was placed at 95° C. for five minutes. The lambda primers and DNA, the "kit" control, were also run as an additional sample for the PCR reagent control (using the manufacturer's recommended reactant concentrations for primers and lambda DNA). A master reaction mix was prepared using the Perkin Elmer-Cetus kit reagents and Taq DNA polymerase (Amplitaq®:Perkin Elmer-Cetus), ([n+1]x15 ul, where n equals the number of test samples) and was heated to 72° C. The master reaction mix was aliquoted (15 ul) to each sample tube, mixed and transferred to the thermal-cycler block which was paused on hold at 72° C. After all samples were added to the thermal-cycler, they were subjected to 15 cycles of 90° C. for 15 sec. (denaturing conditions) and then at 42° C. for 10 sec. (primer annealing conditions). Since the target sequence was short (75 bases), an additional stage for polymerization was not required. Polymerization was accomplished during the ramp up to 90° C. for denaturation (<1° C./sec). After 20 cycles, the reaction was held at 72° C. for the addition of 2.5 ul of the 3' primer (400 nm stock sol.) and 2.5 ul of the 5' primer (400 nM stock sol.). The reactions were subjected to an additional 15 cycles using the same cycling program described above. The reactions were then brought to 65° C. for 45 sec. and then to 4° C., holding for further analysis.

Analysis of Amplification Products

Amplification products were initially analyzed by submarine gel electrophoresis. After the amplification of the 75 base target (the reporter oligonucleotide conjugated to the goat Ab), 15 ul of the amplified sample was mixed with 3 ul of agarose gel loading buffer (30% glycerol and 0.25% bromophenol blue) and analyzed on a 3% agarose gel (8.5x6.0x~0.5 cm:25 ml agarose sol.) containing 0.1 μg/ml ethidium bromide and 0.5x TBE buffer. The gel electrophoresis was carried out by applying 50 V (or 5.9 V/cm) to the gel for 40 min. The results, ethidium bromide-stained DNA bands, were visualized with a UV transilluminator (310 nm wavelength, Model TM-20, UVP, Inc., San Gabriel, Calif.) and recorded on Polaroid type 57 black and white film (Polaroid Corp., Cambridge, Mass.). The bands appeared on the film as white or light gray bands on the dark gray to black background (the gel). Further analysis of amplification products was made by measuring the reflection density of the ethidium bromide stained DNA bands on the Polaroid Type 57 film using a densitometer as cited above. The reflection densitometers were first standardized to standard density plaques that gave specific density reflections in density units. Next the gel background was measured; then the ethidium bromide-stained DNA bands representing each of the amplification product were measured. In this way, the amplification response of each assay was measured, reflecting the amount of antigen present in the sample when compared to a standard curve (a dose-response curve).

Figure 7:
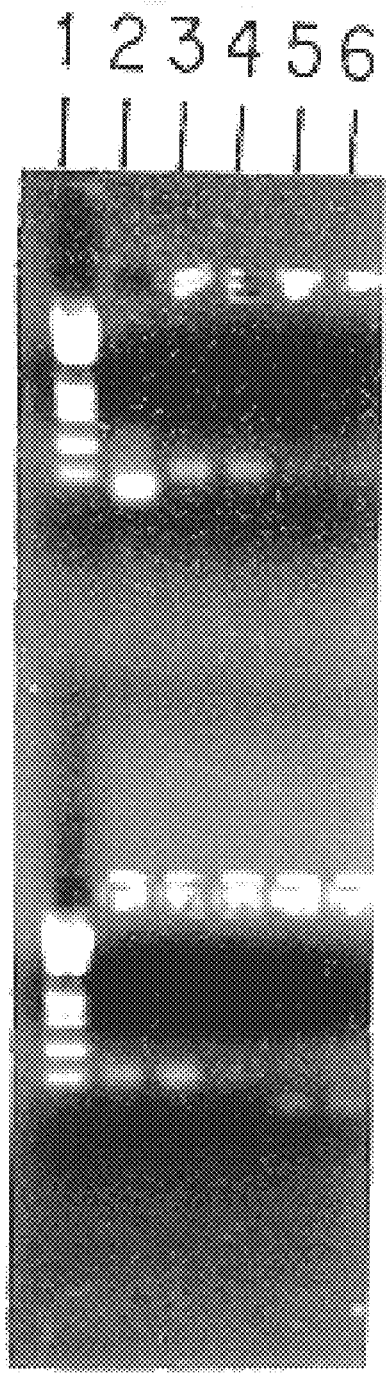
FIG. 7 is a photograph of an electrophoretic agarose gel used to separate the replicated target sequences in a "Direct Target Deposition" assay of the instant invention.

Referring to FIG. 7, lanes 3 through 6 show the amplification response of the 75-base reporter sequence using 0.02 ul of the conjugate in response to different amounts of antigen present in the immunoassay. The samples tested in Lanes 3, 4, and 5 contain 1 ug, 1 ng and 1 pg, respectively. Lane 6 is a control where no analyte was added to test for the amount of non-specific binding (n.s.b.). Lane 1 is Hae III digested Φ X174 molecular weight markers, and lane 2 is λ control primer dimer.

In Table 1 below, the results represent the dose-response of the immunoassay of FIG. 7. Quantitation of the 75-base product was done by measuring the Polaroid 57 film for percent reflectance using the Model RD107R Quanta Log Densitometer. The data expressed as the relative intensity of the ethidium bromide stain (percent reflectance) indicating the assay response as a function of the amount of analyte (Rabbit IgG) present.

TABLE 1

Relative Band Density of Amplification Products Produced in Response to Increasing R-IgG Analyte Concentrations, in the Direct Target Method

| Lane | Amt. of Analyte (R IgG) | Band Density in Percent Reflectance |
| --- | --- | --- |
| 6 | 0 | 9.5 |
| 5 | 1.0 (1 pg) | 10 |
| 4 | 1.0 (1 ng) | 18 |
| 3 | 1.0 (1 ug) | 22 |

As can be seen by the data, assay amplification was achieved when the analyte was present at 1 ng or above.

What is claimed is:

1. A method for simultaneous multiple measurements of a multiplicity of different immobilized non-nucleic acid analytes in a single test sample comprising the steps of:
   i) providing multiple immobilized capture reagents, each comprising at least one member of a binding pair which binds to a nonnucleic acid analyte wherein each capture reagent binds, through said at least one member of the binding pair, to a different non-nucleic acid analyte;
   ii) providing said nonnucleic acid analytes and contacting them with said capture agents to form immobilized non-nucleic acid analytes;
   iii) providing at least one reporter conjugate in the test sample, each conjugate comprising a member of a binding pair conjugated to a unique target nucleic acid sequence wherein each reporter conjugate binds through the member of its binding pair to a unique non-nucleic acid analyte thereby forming analyte-dependent reporter complexes;
   iv) contacting the analyte-dependent reporter complexes with a nucleic acid replication composition capable of replicating said target nucleic acid sequences;
   v) replicating the target nucleic acid sequences; and
   vi) simultaneously detecting the replicated target nucleic acid sequences so as to obtain simultaneous multiple measurements of said unique nonnucleic acid analytes.

2. The method of claim 1, wherein each reporter conjugate is comprised of a binding pair chemically attached to a target nucleic acid sequence.

3. The method of claim 2 wherein each target nucleic acid sequence may be differentiated on the basis of sequence length or sequence identity.

4. The method of claim 3 wherein said target sequences can be replicated by sets of primers that are specific for each target sequence.

5. A method of detecting non-nucleic acid analytes comprising the steps of:
   a) forming an analyte-dependent reporter complex by contacting an immobilized capture reagent which binds to a nonnucleic acid analyte, with a nonnucleic acid analyte, and a reporter conjugate wherein said reporter conjugate is comprised of a member of a binding pair which also binds to the nonnucleic acid analyte and is conjugated to a reporter enzyme;
   b) contacting the analyte-dependent reporter complex with a nucleic acid replication substrate comprising a target nucleic acid sequence conjugated to a moiety capable of detectable activation by said reporter enzyme to produce a detectably activated nucleic acid replication intermediate which deposits onto an immobilized receptor capable of binding to said complex thereby producing a deposited nucleic acid replication product;
   c) contacting the deposited nucleic acid replication product with a nucleic acid replication composition capable of replicating said target nucleic acid sequence;
   d) replicating a target nucleic acid sequence from the deposited nucleic acid sequences
   e) detecting said replicated target nucleic acid sequence.

6. A method of detecting non-nucleic acid analytes comprising the steps of:
   a) forming an analyte-dependent reporter complex by contacting an immobilized capture reagent which binds to a nonnucleic acid analyte, with a nonnucleic acid analyte, and a reporter conjugate wherein said reporter conjugate is comprised of a member of a binding pair which also binds to the nonnucleic acid analyte and is conjugated to a reporter enzyme;
   b) contacting the analyte-dependent reporter complex with a nucleic acid replication substrate comprising a target nucleic acid sequence conjugated to a moiety capable of detectable activation by said reporter enzyme to produce a detectably activated nucleic acid replication intermediate which deposits onto an immobilized receptor capable of binding to said complex thereby producing a deposited nucleic acid replication product;
   c) contacting the deposited nucleic acid replication product with a nucleic acid replication composition capable of replicating said target nucleic acid sequence to produce a deposited nucleic acid replication binding pair complex,
   d) replicating a target nucleic acid sequence of the deposited nucleic acid sequences;
   e) detecting said replicated target nucleic acid sequence.

7. The method of claim 1, further comprising additionally adding to the sample one or more reference nucleic acid sequences and the means for replicating said reference sequences, whereby said reference sequences are replicated in addition to said target sequences and thereby serving as internal controls for more accurate detection and quantitation of more than one non-nucleic acid analyte and wherein the reference nucleic acid sequences are also attached to binding pairs to form reporter conjugates.

8. The method of claim 1, wherein the nucleic acid replication composition provided at step (iv) additionally comprises at least one replication control comprising reference sequences, replicating said reference sequences at step iv) concurrently with at least one of said target sequences and at step v) detecting and separately quantitating the replicated reference sequences and replicated target sequences, to determine a ratio of the concentration of replicated reference sequences to the concentration of replicated target sequences, thereby determining from said ratio the concentration of one or more nonnucleic acid analytes.

9. The method of claim 1 further comprising at step (iii) providing at least one immobilized reference nucleic acid sequence and at step (iv) contacting the reporter complexes with said nucleic acid replication composition wherein said composition additionally comprises the means to replicate the reference sequence of said immobilized reference nucleic acid sequences, at step (v) replicating said reference sequences concurrently with said target sequences and at step (vi) detecting and separately quantitating said replicated reference sequences to determine a ratio of the concentration of the replicated reference sequences to the concentration of replicated target sequences thereby determining from said ratio the concentration of one or more nonnucleic acid analytes.

10. The method of claim 1, 2, 4 or 7, wherein the nucleic acid sequence replication is accomplished using a thermal-stable nucleic acid polymerase.

11. The method of claim 1, 2, 4 or 7, wherein the target or reference nucleic acid sequence contains at one end a first primer binding sequence, and contains at the other end a sequence which is complementary to the first primer binding sequence, thereby enabling replication with a single primer.

12. The method of claim 1, 2, 4 or 7, wherein nucleic acid sequence replication is accomplished using primers which contain sequences at their 5' ends which are not complementary to the target or reference sequences.

13. The method of claim 1, 2, 4 or 7, wherein nucleic acid sequence replication is accomplished using a thermal-stable ligase.

14. The method of claim 1, 2, 4 or 7, wherein at least one signal generating moiety is incorporated within the replicated nucleic acid sequences.

15. The method of claim 14, wherein said signal-generating moieties are radioactive.

16. The method of claim 14, wherein said signal-generating moieties are luminescent.

17. The method of claim 14, wherein said signal-generating moieties are chemiluminescent.

18. The method of claim 14, wherein said signal generating moieties are enzymes.

19. The method of claim 14, wherein said signal generating moieties are fluorescent.

20. The method of claim 19, wherein said fluorescent moieties are positioned within the replicated sequences to enable energy transfer between said fluorescent moieties.

21. The method of claim 19, wherein said fluorescent moieties are positioned no more than about 12 bases apart within the replicated nucleic acid sequences.

22. The method of claim 1, 2, 4 or 7 wherein primers or ligand labeled bases are labeled with a first member of a binding pair are incorporated within the amplified nucleic acid sequences.

23. The method of claim 22, wherein detection and quantitation of the replicated nucleic acid sequences is accomplished by immobilizing the replicated nucleic acid sequences by deposition of said sequences onto an immobilized capture reagent comprising a second member of the binding pair, and further detecting said immobilized replicated nucleic sequences.

24. The method of claim 22, wherein said first member of a binding pair is biotin.

25. The method of claim 1, further comprising after step (iii) separating the replicated nucleic acid sequences from the non-incorporated signal generating moieties using size separation techniques; and (iv) detecting the replicated nucleic acid sequences.

26. A method for the detection and quantitation of a nonnucleic acid analyte or analytes comprising:
   a) adding to an analyte sample an immobilized capture reagent comprising a least one member of a binding pair;
   b) adding simultaneously or sequentially with step (a) at least one ligand reporter conjugate comprising a target nucleic acid sequence conjugated to a ligand wherein the ligand of the reporter conjugate will compete with the analyte for binding to the immobilized capture reagent to form immobilized analyte complexes and/or immobilized ligand complexes;
   c) washing unbound analyte and unbound ligand reporter conjugate away from any immobilized analyte complex and/or immobilized ligand complexes;
   d) contacting washed and immobilized analyte complexes and/or immobilized ligand complexes with a nucleic acid replication composition capable of replicating the target nucleic acid in any of the immobilized ligand complexes;
   e) detecting the presence of replicated target nucleic acid sequences as a means of determining competitive binding of the ligand reporter conjugate and the analyte to the immobilized capture reagent thereby detecting and quantitating the presence of the nonnucleic acid analyte or analytes in the sample.

27. A method for the amplified detection of at least one nonnucleic acid analyte comprising the steps of:
   a) contacting a nonnucleic acid analyte sample with immobilized capture reagent capable of binding to the analyte whereby at least one nonnucleic acid analyte is immobilized;
   b) adding simultaneously or sequentially with step (a) at least one reporter conjugate to the sample wherein said reporter conjugate comprises a target nucleic acid sequence conjugated to a member of a binding pair which is capable of binding, to said nonnucleic acid analyte;
   c) separating any excess reporter conjugates which has remained free in solution from the sample;
   d) contacting free reporter conjugates of step (c) with a nucleic acid replication composition capable of replicating said target nucleic acid;
   e) replicating the target nucleic acid sequence of the free reporter conjugates of step (d);
   f) detecting and quantitating the replicated target nucleic acids of step (e) whereby the presence of at least one analyte in the sample is determined.

* * * * *